US009809767B2

(12) United States Patent
Iaccino et al.

(10) Patent No.: US 9,809,767 B2
(45) Date of Patent: Nov. 7, 2017

(54) $NO_x$ REMOVAL METHOD (71) Applicant: ExxonMobil Chemical Patents Inc., Baytown, TX (US)

(72) Inventors: Larry L. Iaccino, Seabrook, TX (US); Michael Moran, Humble, TX (US); Silvio Carrettin, Kraainem (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 119 days.

(21) Appl. No.: 14/434,243

(22) PCT Filed: Nov. 7, 2013

(86) PCT No.: PCT/US2013/068831
§ 371 (c)(1),
(2) Date: Apr. 8, 2015

(87) PCT Pub. No.: WO2014/078153
PCT Pub. Date: May 22, 2014

(65) Prior Publication Data
US 2015/0267131 A1 Sep. 24, 2015

Related U.S. Application Data (60) Provisional application No. 61/726,796, filed on Nov. 15, 2012.

(30) Foreign Application Priority Data

Jan. 16, 2013 (EP) .................................... 13151521

(51) Int. Cl.
*C10G 45/00* (2006.01)
*C07C 5/327* (2006.01)
(Continued)

(52) U.S. Cl.
CPC ........... *C10G 70/046* (2013.01); *B01D 53/04* (2013.01); *B01D 53/26* (2013.01); *B01D 53/56* (2013.01);
(Continued)

(58) Field of Classification Search
CPC .... Y02P 30/464; F25J 3/0238; F25J 2215/62; F25J 3/064; F25J 2210/12; F25J 3/0625;
(Continued)

(56) References Cited

U.S. PATENT DOCUMENTS

| 5,955,045 A | * | 9/1999 | Baur | .................... B01D 53/565 208/254 R |
| 2010/0000911 A1 | * | 1/2010 | Rudolf | ............... B01D 53/8625 208/254 R |

FOREIGN PATENT DOCUMENTS

| DE | 4012982 | 10/1991 |
| EP | 862938 | 9/1998 |

(Continued)

OTHER PUBLICATIONS

Carbon, 1996, 34(8), 1027-1033.
(Continued)

*Primary Examiner* — Anthony J Zimmer
*Assistant Examiner* — Syed Iqbal (57) ABSTRACT The invention relates to mixtures comprising molecular hydrogen, hydrocarbons, and nitrogen oxides; to processes for removing at least a portion of the nitrogen oxides therefrom; to equipment useful in such processes; and to the use of such hydrocarbons for, e.g., chemical manufacturing.

24 Claims, 4 Drawing Sheets

(51) Int. Cl.

| | | |
|---|---|---|
| *C10G 11/00* | (2006.01) | |
| *C10G 70/02* | (2006.01) | |
| *C10G 70/04* | (2006.01) | |
| *C01B 3/50* | (2006.01) | |
| *B01D 53/04* | (2006.01) | |
| *C10G 70/00* | (2006.01) | |
| *F25J 3/06* | (2006.01) | |
| *F25J 3/02* | (2006.01) | |
| *B01D 53/56* | (2006.01) | |
| *B01D 53/047* | (2006.01) | |
| *B01D 53/14* | (2006.01) | |
| *B01D 53/26* | (2006.01) | |

(52) U.S. Cl.
CPC .............. *B01D 53/565* (2013.01); *C01B 3/50* (2013.01); *C07C 5/327* (2013.01); *C10G 11/00* (2013.01); *C10G 45/00* (2013.01); *C10G 70/00* (2013.01); *C10G 70/02* (2013.01); *C10G 70/043* (2013.01); *C10G 70/047* (2013.01); *F25J 3/0223* (2013.01); *F25J 3/0233* (2013.01); *F25J 3/0238* (2013.01); *F25J 3/0252* (2013.01); *F25J 3/064* (2013.01); *F25J 3/0625* (2013.01); *F25J 3/0635* (2013.01); *F25J 3/0655* (2013.01); *B01D 53/047* (2013.01); *B01D 53/0462* (2013.01); *B01D 53/1456* (2013.01); *B01D 53/261* (2013.01); *B01D 2257/40* (2013.01); *B01D 2257/80* (2013.01); *B01D 2259/402* (2013.01); *B01D 2259/40088* (2013.01); *B01D 2259/416* (2013.01); *C01B 2203/048* (2013.01); *C01B 2203/0465* (2013.01); *F25J 2205/04* (2013.01); *F25J 2205/60* (2013.01); *F25J 2205/66* (2013.01); *F25J 2210/12* (2013.01); *F25J 2215/62* (2013.01); *F25J 2220/02* (2013.01); *F25J 2270/04* (2013.01); *Y02P 30/464* (2015.11)

(58) Field of Classification Search
CPC ...... F25J 3/0635; F25J 3/0655; F25J 2205/66; F25J 3/0252; F25J 2205/60; F25J 2205/04; F25J 3/0233; F25J 2220/02; F25J 3/0223; F25J 2270/04; C10G 11/00; C10G 70/043; C10G 70/047; C10G 45/00; C10G 70/046; C10G 70/00; C10G 70/02; B01D 53/1456; B01D 53/56; B01D 53/047; B01D 53/04; B01D 53/261; B01D 53/26; B01D 2257/80; B01D 2259/402; B01D 2257/40; B01D 2259/416; B01D 53/0462; B01D 53/565; C01B 2203/0465; C01B 2203/048; C07C 5/327

See application file for complete search history.

(56) References Cited

FOREIGN PATENT DOCUMENTS

| JP | 07178316 | 7/1995 |
|---|---|---|
| JP | 08299756 | 11/1996 |

OTHER PUBLICATIONS

Atmospheric Environment 1987, 21(9), 2053-2055.
Separation Science and Technology 2002, 37(4) 937-956.
Journal of Materials Science, 2008 43(19), 6505-6512.
Studies in Surface Science and Catalysis 2006, 159, 229-232.
Langmuir 2001, 17, 4997.
Appl. Cat B: Env. 2009, 88(1-2), 113-126.
J. Chem. Soc. Faraday Trans., 1995, 91(3), 517-524.
Applied Catalysis A: General, 197 (1), 2000, 69-78.
Huanjing Huaxue, 1996, 15(4), 289-295.
Transactions of the Materials Research Society of Japan, 1994, 18A, 401-404.
Catalysis Today (1999) 54(4) 547-552.
K. Pansanga, et al., Applied Catalysis A: General 332 (2007) 130-137.

* cited by examiner

NO$_x$ REMOVAL METHOD

CROSS-REFERENCE OF RELATED APPLICATIONS

Priority Claim

This application is a National Stage Application of International Application No. PCT/US2013/068831, filed Nov. 7, 2013, which claims the priority to and the benefit of U.S. Provisional Application Nos. 61/726,796, filed Nov. 15, 2012, and European Application No. 13151521.5, filed Jan. 16, 2013, the disclosures of which are fully incorporated herein by their reference.

FIELD OF THE INVENTION

The invention relates to mixtures comprising molecular hydrogen, hydrocarbons, and nitrogen oxides; to processes for removing at least a portion of the nitrogen oxides therefrom, to equipment useful in such processes; and to the use of such hydrocarbons for, e.g., chemical manufacturing.

BACKGROUND OF THE INVENTION

Hydrocarbon upgrading and conversion processes such as catalytic cracking, pyrolysis, hydroprocessing, reforming, and the like can be utilized for producing mixtures comprising molecular hydrogen, methane, and other hydrocarbons. It is generally desirable to separate methane and molecular hydrogen from the mixture, e.g., utilizing boiling-point separation. For example, vapor mixtures comprising molecular hydrogen and methane can be exposed to a relatively low temperature in order to condense a stream comprising at least a portion of the mixture's methane. The condensed methane can then be separated from the molecular hydrogen, which remains in the vapor phase. Such separations can be carried out in a system of integrated heat exchangers and separation drums, e.g., a conventional cold box.

One difficulty encountered in such low-temperature separations involves the accumulation in a cold box or other low-temperature region of gums and/or salts of compounds comprising oxygen and nitrogen ("NO$_x$"). NO$_x$ gums, which result from the reaction of NO$_x$ with hydrocarbons, have been observed to react in an uncontrolled manner (e.g., explosively) at sub-ambient temperatures, such as those temperatures encountered when a cold box is warmed for maintenance, shutdown, unplanned temperature excursion (resulting, e.g., from process gas compressor failure, refrigeration system failure, etc.), and the like. The accumulation of NO$_x$ salts represents a similar concern because these can also react in an uncontrolled manner, albeit at higher temperature than that of NO$_x$ gums (e.g., at or near ambient temperatures), and can contribute to the total energy released during an uncontrolled reaction initiated by NO$_x$ gums.

The accumulation of NO$_x$ gums and salts can be lessened by removing NO$_x$ compounds downstream of a hydrocarbon upgrading or conversion process but upstream of low-temperature region utilized for methane condensation and separation. For example, U.S. Pat. No. 5,955,045 discloses a method for the selective chemisorption of NO$_x$ compounds, such as those found in the waste gas of a fluidized catalytic cracking unit. In an example, the patent discloses an NO removal rate of 85% after an operating time of more than 130 hours by exposing a mixture comprising methane, molecular hydrogen, and 20 mol ppb of NO to a catalyst comprising MnO$_2$ on Al$_2$O$_3$ at a space velocity of about 4000 h$^{-1}$. Utilizing relatively low-capacity adsorbents at a relatively low space velocity provides a relatively long run length before adsorbent regeneration is needed.

It is desired to improve NO$_x$-removal technology, e.g., by utilizing higher space velocities and/or NO$_x$ removal agents having increased capacity, in order to remove an even greater amount of NO$_x$ removed from mixtures containing methane, molecular hydrogen, and optionally, water and other saturated and/or unsaturated hydrocarbons.

SUMMARY OF THE INVENTION

Certain aspects relate to a process or removing NO$_x$ from a hydrocarbon-containing stream (a "first stream"), the first stream is produced comprising ≥1.0 wt. % methane, ≥1.0 wt. % molecular hydrogen, and ≥2.0 ppbw of NO$_x$, the weight percents being based on the weight of the first stream. An upgraded first stream by exposing the first stream during a first time interval to a first removal agent to remove ≥50.0 wt. % of the first stream's NO$_x$, based on the weight of the stream's NO$_x$. The first stream contacts the first removal agent at a space velocity (GHSV)≥2.5×10$^4$ hr$^{-1}$, such as ≥5.0×10$^4$ hr$^{-1}$. The upgraded first stream can be exposed to a temperature sufficient to condense at least a portion of the first stream's methane, to disengage the condensed methane from the remainder of the upgraded first stream. Second and third streams can be conducted away from the process, wherein the second stream comprises at least a portion of the condensed methane and the third stream comprises at least a portion of the upgraded first stream's molecular hydrogen. At the end of the first time interval, the flow of the first stream can be lessened or diverted away from the first removal agent. During a second time interval following the first time interval the first removal agent can be at least partially regenerated, so that it can be re-used.

Utilizing a NO$_x$ removal agent that can operate at a space velocity (GHSV)≥2.5×10$^4$ hr$^{-1}$ can enable the removal of water and NO$_x$ from a hydrocarbon stream, e.g., during substantially the same time interval. Accordingly, other aspects of the invention relate to an upgrading process utilizing first and second removal agents, the first removal agent being effective for removing NO$_x$ from and the second removal agent being effective for removing water. The first and second removal agents can be located in the same vessel. The process can include the steps of
  (a) providing a first stream comprising ≥10.0 wt. % methane, ≥1.0 wt. % of molecular hydrogen, ≥2.0 ppbw of NO$_x$, and ≥1.0 wt. % water, the weight percents being based on the weight of the first stream; and
  (b) during a first time interval exposing the first stream to
    (i) a second removal agent to remove ≥50.0 wt. % of the first stream's water based on the weight of the first stream's water and (ii) to a first removal agent to remove ≥50.0 wt. % of the first stream's NO$_x$ based on the weight of the stream's NO$_x$ to produce a first upgraded mixture, wherein the first stream contacts the first removal agent at a space velocity (GHSV)≥2.5× 10$^4$ hr$^{-1}$, such as ≥5.0×10$^4$ hr$^{-1}$.

Other aspects of the invention relate to a process for separating a methane-rich stream and a molecular hydrogen-rich stream from a first stream, the process comprising:
  (a) providing the first stream, the first stream comprising ≥1.0 wt. % water, ≥10.0 wt. % methane, ≥1.0 wt. % molecular hydrogen, and ≥2.0 ppbw of NO$_x$, the weight percents being based on the weight of the first stream;

(b) producing a first upgraded stream by exposing at least a first portion of the first stream during a first time interval to (i) a second removal agent to remove ≥50.0 wt. % of the first stream's water, based on the weight of the first stream's water, and (ii) a first removal agent to remove ≥50.0 wt. % of the first stream's $NO_x$, based on the weight of the stream's $NO_x$, wherein the first stream contacts the first removal agent at a space velocity (GHSV)≥2.5×10$^4$ hr$^{-1}$, such as ≥5.0×10$^4$ hr$^{-1}$;

(c) at least partially regenerating the first and second removal agents during a second time interval following the first time interval;

(d) conducting at least a portion of the first upgraded stream to a cold box, the cold box being operated under conditions sufficient to condense at least a portion of the first upgraded stream's methane;

(e) removing a second stream from the cold box, the second stream being the methane-rich stream which comprises at least a portion of the condensed methane; and (f) removing a third stream from the cold box, the third stream being the molecular hydrogen-rich stream which comprises at least a portion of the first upgraded stream's molecular hydrogen.

DETAILED DESCRIPTION OF THE INVENTION

Figure 1:
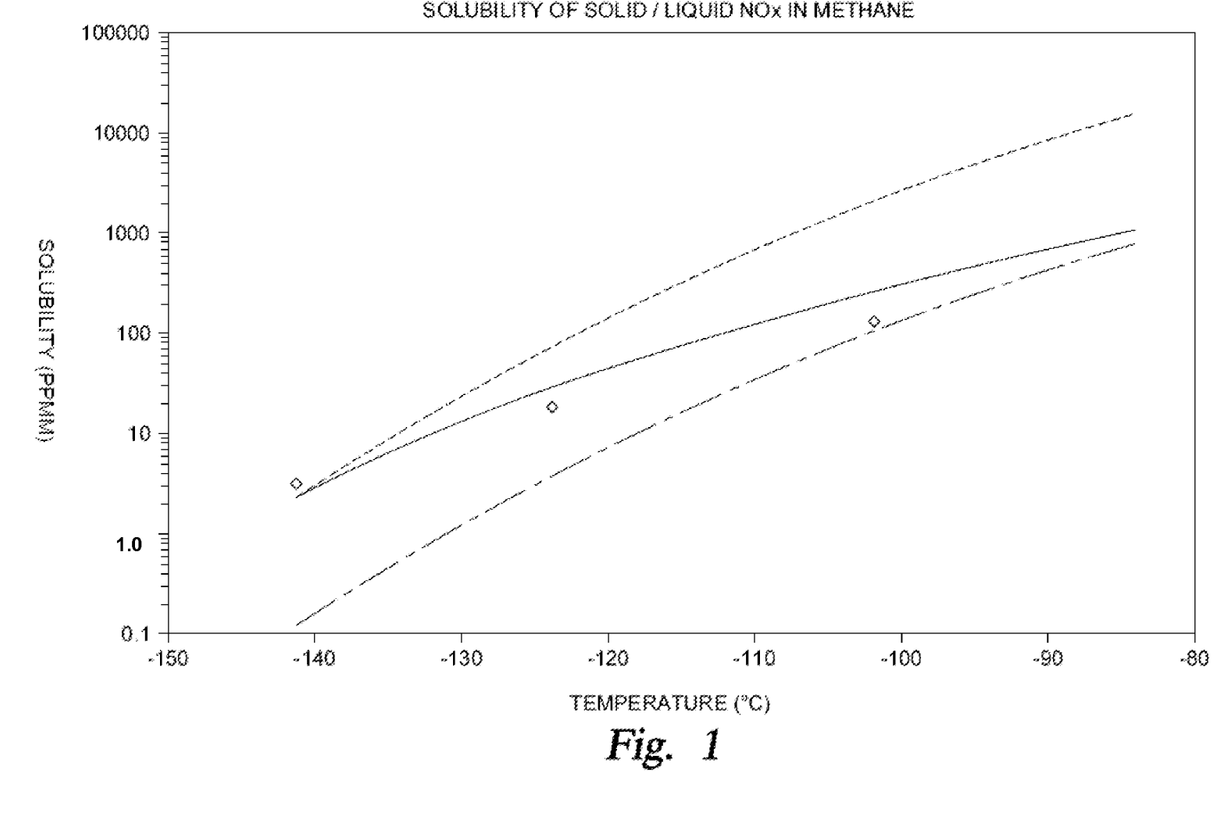
FIG. 1 is a chart illustrating the solubility versus temperature for solid or liquid $NO_x$ in a $NO_x$-methane mixture.

Measurements of solid-liquid equilibrium of $NO_x$ compounds in methane are well-correlated with $NO_x$ solubility models. See, e.g., FIG. 1, which shows modeling results for the solubility of $N_2O_3$ (short dashes), $NO_2$ (solid line), and $N_2O_4$ (long dashes), and solubility data for $NO_2$ (diamonds). These results would lead one to conclude that $NO_x$ compounds would not accumulate in a low-temperature molecular hydrogen-methane separation system, e.g., a cold box, provided $NO_x$ amounts are maintained at ≤1 ppm (molar basis, written as "ppmm") at temperatures higher (warmer) than −200° F. (−129° C.). The invention is based in part on the discovery that maintaining $NO_x$ amounts at such a level is not sufficient to prevent $NO_x$ accumulation in a low-temperature molecular hydrogen-methane separation system.

It has now been observed that $NO_x$ levels as small as 5 ppb (weight basis, written as "ppbw") can lead to accumulation of $NO_x$ compounds. It is believed that this results at least in part from surface adsorption of $NO_x$ compounds, e.g., on metallic surfaces within the cold box. For example, an analysis of data obtained from commercial cold box systems indicates that even $NO_x$ concentrations that would be considered small by commercial standards (e.g., about 250 ppbw) leads to an unacceptable rate of $NO_x$ compound accumulation. This discovery has led to the development of processes, systems, and equipment for removing $NO_x$ to achieve an amount <5 ppbw (equivalent to <about 2.7 ppbm for a $NO_x$-methane mixture) or <3 ppbw (equivalent to <about 1.6 ppbm for a $NO_x$-methane mixture), or even lower, such as ≤2.0 ppbw, or even ≤1.0 ppbw.

Although much of the prior art focuses on $NO_2$ removal, it has now been observed that ≥50.0 wt. % of $NO_2$ in a molecular-hydrogen-methane mixture will be conducted away from a cold box, e.g., in liquid streams transferred from the cold box to a demethanizer; such as ≥75.0 wt. % or even ≥90.0 wt. % based on the weight of the $NO_2$ in the molecular hydrogen-methane mixture. In other words, $NO_2$ will exit the cold box prior to reaching the sections of the cold box having a sufficiently low temperature for $NO_x$ gums to form. Since an appreciable amount of NO is not conducted away from the separator with the $NO_2$, certain embodiments of the invention relate to selectively removing NO from streams conducted to low-temperature separation systems.

Figure 2:
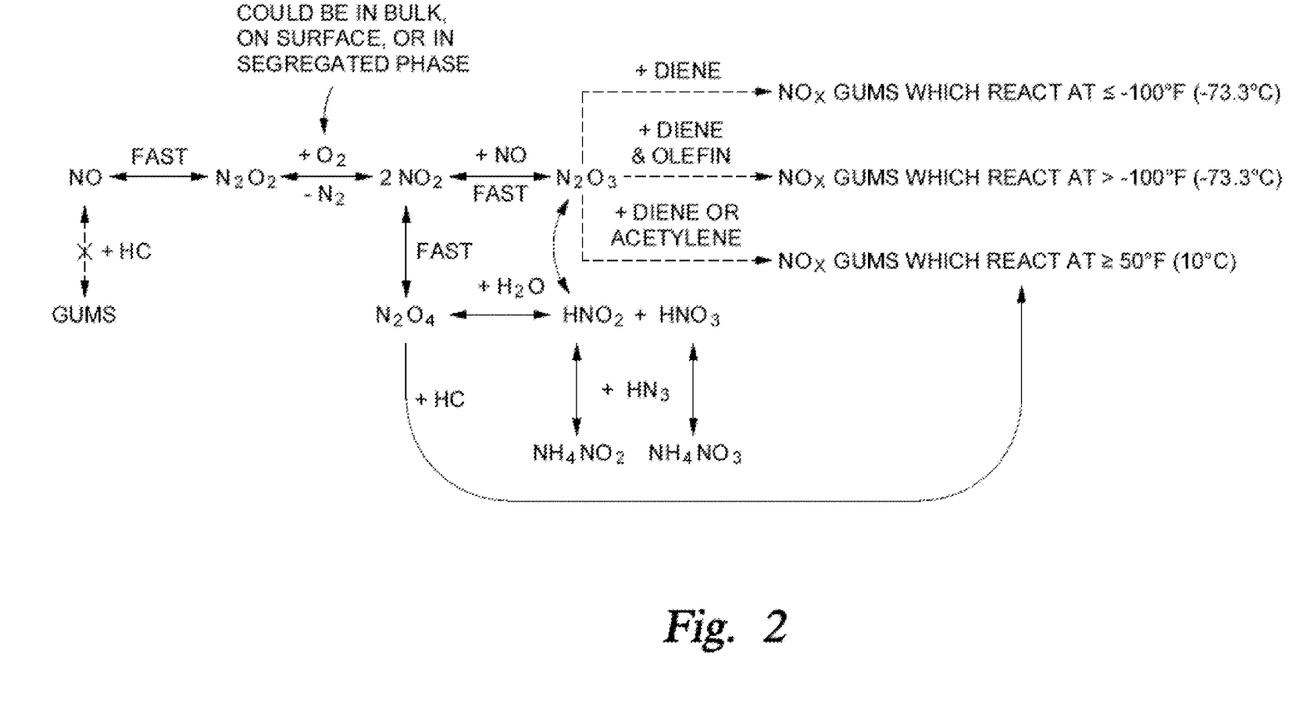
FIG. 2 schematically illustrates reaction pathways that are believed to predominate for the formation of $NO_x$ gums, which can react in an uncontrolled manner at the designated temperature.

While not wishing to be bound by any theory or model, it is believed that $NO_x$ produces $NO_x$ gums in low-temperature separation systems primarily according to the chemical pathways schematically illustrated in FIG. 2. Instead of the direct formation of $NO_x$ gums by the relatively slow reaction of hydrocarbon with NO in the separator, the much faster reaction pathways involving $N_2O_2$ predominate. For example, FIG. 2 schematically shows that $N_2O_2$ produces $NO_2$, which can then react with (i) NO to form $N_2O_3$ (which reacts with dienes to form $NO_x$ gums) and/or (ii) itself to form $N_2O_4$ which leads to the formation of $NO_x$ gums (via a reaction with hydrocarbon) and $NO_x$ salts via a reaction with water. Accordingly, aspects of the invention are based on removing sufficient $NO_x$ from the low-temperature separator's feed stream to lessen the formation of oxidized NO molecules. In other words, certain aspects relate to lessening the amount of $NO_x$ gum and $NO_x$ salt formation by maintaining the amount of $NO_x$, e.g., the amount of NO, in the upgraded first stream at an amount that is <5.0 ppbw or <3.0 ppbw, or even lower, such as ≤2.0 ppbw, or even ≤1.0 ppbw. Other aspects relate to an improved process for removing water from the upgraded first stream by substituting at least one $NO_x$ removal agent for a portion of the water removal agent.

Selected aspects will now be described in more detail. The invention is not limited to these and this description is not meant to foreclose other aspects/embodiments within the broader scope of the invention. For the purpose of this description and appended claims, the following definitions will be utilized.

A "cold box" is a system of integrated heat exchangers and vapor liquid separators to produce at least (i) a stream rich in molecular hydrogen ("$H_2$"), (ii) a stream rich in methane, and optionally (iii) one or more streams rich in hydrocarbons having a molecular weights that are greater than or equal to that of acetylene ($C_{2+}$).

The term "NO removal" means at least the partial removal of NO molecules from a mixture comprising molecular hydrogen and hydrocarbon (e.g., methane), and can encompass adsorption, absorption, and/or chemical transformation. In certain embodiments, sufficient NO removal occurs to achieve an NO amount in a cold box's feed stream of ≤5.0 ppbw, e.g., ≤3.0 ppbw, such as ≤2.0 ppbw, or preferably ≤1.0, or more preferably ≤0.5 ppbw of NO based on the weight of NO in the cold box's feed stream.

The term "$NO_x$" means NO, $NO_2$, $N_2O_2$, $N_2O_3$, $N_2O_4$, and oxidized nitrogen oxide molecules of higher order.

The term "$NO_x$ gum(s)" means reaction products of $NO_x$ with hydrocarbons.

The term "$NO_x$ salt(s)" means at least one $NO_x$ ion bound to at least one counterion.

The term "$NO_x$ compounds" means chemical compounds including at least one $NO_x$ unit, e.g., $NO_x$ gums and $NO_x$ salts (such as ammonium nitrate and ammonium nitrite).

The term "tail gas" means a methane-rich stream containing molecular hydrogen. Tail gas includes those methane-rich streams obtained from one or more cold boxes and/or streams and/or those obtained in the course of molecular hydrogen purification, such as by pressure swing adsorption and/or membrane separation. Tail gas generally does not contain an appreciable amount of water or $NO_x$, e.g., ≤1 ppmw of water and/or ≤1 ppmw of $NO_x$, based on the weight of the tail gas.

The term "space velocity" means gas hourly space velocity ("GHSV"), where GHSV is equal to the volume of feed contacting a volume of $NO_x$ removal agent per hour. GHSV is calculated at STP (0° C. and 1 bar) from $NO_x$ removal agent density (mass of $NO_x$ removal agent per packed volume of $NO_x$ removal agent) and feedstream component amounts and densities.

The term "$C_{2+}$" means compounds containing two or more carbon atoms, e.g., ethane. The term "$C_{2+}$ unsaturates" means compounds containing two or more carbon atoms, wherein at least two of the compound's carbon atoms are joined by a double or triple bond.

Certain aspects of the invention relate to separation processes, e.g., processes for upgrading a mixture comprising hydrocarbon and molecular hydrogen, by way of one or more separations. For example, the process can include (a) providing a first stream, the first stream comprising ≥1.0 wt. % methane, ≥1.0 wt. % molecular hydrogen, and ≥2.0 ppbw of $NO_x$, the weight percents being based on the weight of the first stream; and (b) producing an upgraded first stream by exposing the first stream during a first time interval to a first removal agent to remove ≥50.0 wt. % of the first stream's $NO_x$, based on the weight of the mixture's $NO_x$, wherein the first stream contacts the first removal agent at a space velocity (GHSV)≥2.5×10$^4$ hr$^{-1}$. The processes can also include, e.g., at least partially regenerating the first removal agent during a second time interval following the first time interval. If desired, the upgraded first stream can be conducted away, or further processed, e.g., during the first interval or thereafter. Optionally, the process includes exposing the upgraded first stream to a temperature sufficient to condense at least a portion of the first stream's methane, and conducting a second stream away from the process, the second stream comprising at least a portion of the condensed methane. Generally, the temperatures utilized for condensing methane are insufficiently cold to condense the upgraded first stream's molecular hydrogen. Optionally, at least a portion of the upgraded first stream's molecular hydrogen is conducted away from the process, e.g., as a third stream, which can be in the vapor phase. The first stream will now be described in more detail. The invention is not limited to this first stream and this description is not meant to foreclose other first streams within the broader scope of the invention.

The First Stream

The first stream can be a mixture (and can referred to as a "first mixture") obtained from one or more hydrocarbon upgrading and conversion processes such as catalytic cracking, pyrolysis, hydroprocessing, reforming, etc. Referring to the first mixture as a "stream" is not meant to exclude other embodiments within the broader scope of the invention, such as those where the mixture does not flow continuously, as might be the case in e.g., batch or semi-continuous processes. Aspects of the process are advantageous for upgrading mixtures obtained from the fluidized catalytic cracking of hydrocarbons, particularly those containing a significant amount of $NO_x$. Optionally, the first stream is subjected to initial processing, e.g., one or more pre-treatment steps, before it is subjected to $NO_x$ removal. Such pre-treatments can include, e.g., one or more of selective hydrogenation, sulfur compound removal, mercury removal, heavier hydrocarbon removal, water removal, $CO_2$ removal, or CO removal.

When the first stream is a feed to a low-temperature separation stage, such as a cold box, it is referred to as a "feed stream". The first stream can be provided to the process continuously, semi-continuously, or batch mode, depending on the configurations of the process equipment and separation systems utilized.

Suitable first streams include, e.g., those which comprise methane, molecular hydrogen, and ≥2.0 ppbw of $NO_x$ based on the weight of the first stream. In addition to the methane and the molecular hydrogen, the first stream can further comprise water and additional hydrocarbon such as $C_{2+}$ hydrocarbon, and in particular, $C_{2+}$ unsaturates, such as one or more of acetylene, ethylene, or propylene. For example, the first stream can comprise ≥10.0 wt. % methane ≥0.1 wt. % molecular hydrogen, and ≥2.0 ppbw $NO_x$, the weight percents being based on the weight of the first stream; and can optionally further comprise ≥1.0 wt. % of $C_{2+}$ hydrocarbons (e.g., $C_{2+}$ olefin) and ≥0.1 ppmw of water. Such first streams include those comprising 20.0 wt. % to 80.0 wt. % methane, 0.5 wt. % to 20.0 wt. % molecular hydrogen, 1.0 wt. % to 80.0 wt. % $C_2$ unsaturates, 2.0 ppbw to 1.0×10$^3$ ppmw of NO, and optionally further comprising one or more of 1 ppmw to 10.0 wt. % water, 1.0 ppbw to 1.0×10$^3$ ppmw of $NO_2$, ethane, propylene, butadiene, $C_{3+}$ saturates, mercury, CO, or $CO_2$. Optionally, the first stream has a molecular weight in the range of 10.0 grams/mole to 35.0 grams/mole, e.g., 15.0 grams/mole to 30.0 grams/mole.

In certain embodiments, ≥50.0 wt. % of the first stream's $C_{2+}$ unsaturates are produced by one or more of pyrolysis, cracking, reforming, hydrogen transfer, or the regeneration of at least partially-coked catalyst, based on the weight of the first stream's $C_{2+}$ unsaturates. Optionally, the first stream has an acetylene: ethylene molar ratio ≤1.0.

In certain aspects, the first stream has a molecular weight in the range of 16.0 to 27.0, wherein 100 mole of the first stream comprises 10.0 mole to 50.0 mole of molecular hydrogen, 5.0 mole to 30.0 mole of methane, 0.05 mole to 35.0 mol of ethylene, 5.0 mole to 20.0 mole of ethane, 0.1 mole to 15.0 mole of propylene, 4×10$^{-4}$ mole to 3.0 mole of butadiene, 0.1 mole to 25 mole of $C_{3+}$ saturates, and ≥3.0 ppbm NO, with the balance being, e.g., one or more of water, carbon monoxide, carbon dioxide, sulfur-containing compounds, mercury and/or mercury-containing compounds, metals, coke, particulates, or nitrogen oxides of higher order, such as ≥1.0 ppbm of $NO_2$. When the first stream contains NO and/or $NO_2$, (i) the amount of NO is optionally in the range of 5.0 ppbw to 1.0 wt. %, e.g., 10.0 ppbw to 1.0×10$^3$ ppmw, such as 1.0×10$^2$ ppbw to 1.0×10$^2$ ppmw, based on the weight of the first stream; and (ii) the amount of $NO_2$ is optionally in the range of 1.0 ppbw to 1.0 wt. %, e.g., 10.0 ppbw to 1.0×10$^3$ ppmw, such as 1.0×10$^2$ ppbw to 1.0×10$^2$ ppmw, based on the weight of the first stream.

The first stream can be converted to an upgraded first stream by exposing the first stream during a first time interval to a first removal agent to remove ≥50.0 wt. % of the first stream's $NO_x$, based on the weight of the mixture's $NO_x$, wherein the first stream contacts the first removal agent at a space velocity (GHSV)≥$2.5 \times 10^4$ $hr^{-1}$. One skilled in the art will appreciate that the first stream's composition will change during the $NO_x$ removal, and the compositions specified in this section of the description refer to the first stream as it subsists at the start of the $NO_x$ removal.

Aspects relating to removing $NO_x$ and producing the upgraded first stream will now be described in more detail. The invention is not limited to these aspects and this description is not meant to foreclose other aspects/embodiments for producing the upgraded first stream within the broader scope of the invention.

$NO_x$ Removal

The amount of $NO_x$ in the first stream can be lessened by contacting the first stream with at least one $NO_x$ removal agent. For example, the first stream can be conducted to one or more vessels, with each vessel containing (i) at least one $NO_x$ removal agent and optionally (ii) one or more additional removal agents for removing other constituents of the first stream, such as water. Process conditions in the vessel(s) are generally controlled to provide conditions of temperature, pressure, flow, etc., that are effective for removing $NO_x$ from the first stream. When more than one vessel is used, the vessels can be arranged on series, parallel, or a combination thereof. The $NO_x$ removal agents can be, e.g., in the form of a discrete layer, such as a packed bed located within a region of the vessel, with other regions of the vessels utilized for other purposes, e.g., for water removal.

The vessels can further comprise one or more additional agents for the removal of water, mercury, sulfur compounds, and/or other contaminants. Accordingly, certain aspects relate to removal agents that are combined such that the $NO_x$ and water, mercury, sulfur compounds, and/or other contaminants are removed by the same bed in the vessel. For example, the bed can comprise a plurality of removal agents, or the removal agent may be in different locations in a vessel or may be layered upon each other or within the vessel. For example, the $NO_x$ removal agent can be located in a discrete layer, the discrete layer being situated proximate to the outlet of the vessel—the outlet being with respect to the flow of the first stream while in $NO_x$ removal mode of operation (i.e., not regeneration mode).

The $NO_x$ removal can include exposing the first stream to at least one $NO_x$ removal agent under $NO_x$ removal conditions, the $NO_x$ removal conditions including one or more of a temperature in the range of 4.0° C. to 50.0° C., a pressure in the range of 13 bar (absolute) to 40 bar (absolute), and a space velocity (GHSV)≥$2.5 \times 10^4$ $hr^{-1}$. Optionally, the first stream is exposed to the $NO_x$ removal agent for a time interval (e.g., a first time interval) that is ≥0.01 hours, or ≥0.1 hours, or ≥1.0 hours, but ≤10,000 hours, or ≤1000 hours or ≤100 hours. In certain embodiments, the time interval is in the range of from 5 hours to 500 hours, or 20 hours to 500 hours, e.g., 50 to 200 hours, such as 70 to 150 hours, or 80 to 100 hours. For example, the time interval can be in the range of from 10 hours to 200 hours, such as 15 hours to 100 hours, or 20 hours to 60 hours. It is observed that when the $NO_x$ removal agent is selected from among those that can remove $NO_x$ effectively at a GHSV≥$2.5 \times 10^4$ $hr^{-1}$, the first time interval encompasses durations that are known to be effective for removing water from representative first streams under conventional water-removal conditions. This observation has led to the development of certain aspects of the invention, including those where a $NO_x$ removal agent is substituted for a minor amount of a drier vessel's water removal agent.

An upgraded first stream is generally conducted away from the $NO_x$ removal step, e.g., conducted away from a vessel containing the $NO_x$ removal agent. The upgraded first stream has less $NO_x$ than does the first stream. For example, the upgraded first stream generally has a $NO_x$ content that is ≤0.90 times the first stream's $NO_x$ content on a weight basis, such as ≤0.75 times, or ≤0.50 times, or even ≤0.25 times. In other words, ≥25.0 wt. % of the first stream's $NO_x$ is removed during the $NO_x$ removal step, based on the weight of the first stream's $NO_x$, e.g., ≥50.0 wt. %, or ≥75.0 wt. %, or ≥90.0 wt. %, or even ≥99.0 wt. %. In certain embodiments, ≥25.0 wt. % of the first stream's NO is removed during the $NO_x$ removal step, based on the weight of the first stream's NO, e.g., ≥50.0 wt. %, or ≥75.0 wt. %, or ≥90.0 wt. %, or even ≥99.0 wt. %.

In certain embodiments, the upgraded first stream has a $NO_x$ content that is ≤100 ppbw. For example, the $NO_x$ content can be ≤5.0 ppbw, e.g., ≤3.0 ppbw, such as ≤1.0 ppbw, based on the weight of the upgraded first stream's $NO_x$. The upgraded first stream can have an NO content that is ≤5.0 ppbw, e.g., ≤3.0 ppbw, such as ≤1.0 ppbw, based on the weight of the upgraded first stream's NO. When water is also removed from the first stream, the upgraded first stream can comprise, e.g., ≥10.0 wt. % methane, ≥1.0 wt. % of $C_2$ unsaturates, ≤1.0 ppbw of $NO_x$, the weight percents being based on the weight of the upgraded first stream, and can further comprise ≤0.1 mole of water per mole of the upgraded first stream. Optionally, the upgraded first stream comprises ≤1.0 ppmw water, based on the weight of the first stream.

$NO_x$ Removal Agent

The $NO_x$ removal step utilizes one or more $NO_x$ removal agents, e.g., one or more agent that removes $NO_x$ by (i) absorption or adsorption, such as by chemisorption and/or physisorption, and/or (ii) chemically reacting the $NO_x$, such as via a redox reaction. Suitable $NO_x$ removal agents include those capable of removing ≥25.0%, e.g, ≥50.0%, such as ≥75.0%, or even ≥90.0% (weight basis) of $NO_x$ from a hydrocarbon-containing stream at a GHSV≥$2.5 \times 10^4$ $hr^{-1}$, such as ≥$5.0 \times 10^4$ $hr^{-1}$. Non-limiting examples of suitable $NO_x$ removal agents include (i) those capable of oxidizing $NO_x$, such as those capable of oxidizing NO to $NO_2$ (and subsequently removing the $NO_2$) and (ii) those capable of reducing $NO_x$, such as those capable of reducing NO to $N_2$ and $O_2$ or to a metal oxide. The invention is not limited to these NO removal agents, and this description is not meant to foreclose other $NO_x$ removal agents within the broader scope of the invention.

It is generally desirable for the $NO_x$ removal agent to have one or more of the following properties:

(i) When the first stream comprises $C_{2+}$, e.g., ≥1.0 wt. % of $C_{2+}$ based on the weight of the first stream, the $NO_x$ removal agent should not hydrogenate an appreciable amount of the first stream's $C_{2+}$ unsaturates, and in particular should not hydrogenate an appreciable amount of the first stream's ethylene or propylene. The term "appreciable amount" in this context means that ≥20 mole % of the first stream's ethylene is hydrogenated to ethane, e.g., ≥25 mole %, such as ≥30 mole %, the mole percents being based on 100 mole % of the ethylene in the first stream. Optionally, the $NO_x$ removal agent should hydrogenate ≤50.0 wt. % of the first stream's ethylene based on the weight of the first stream's ethylene, such as ≤25.0 wt. %, or ≤10.0 wt. %, or even ≤1.0 wt. %. For example, the upgraded first stream's acetylene: ethylene and/or ethylene: ethane molar ratios are generally within about +/−10% of those of the first stream, such as +/−1%.

(ii) The $NO_x$ removal agent should not produce an appreciable amount of heavier hydrocarbon oligomers when contacting the first stream. The term "appreciable amount" in this context means ≤5 wt. % of the upgraded first stream (based on the weight of the upgraded first stream) comprises $C_{10+}$ that is produced during the $NO_x$ removal, e.g., ≤1 wt. %, such as ≤0.1 wt. %. Optionally, the $NO_x$ removal agent converts ≤1.0 wt. % of the first stream's hydrocarbon to oligomers of order two or higher, based on the weight of the first stream's hydrocarbon, such as ≤0.1 wt. %.

(iii) The $NO_x$ removal agent should not have a high heat of adsorption when switching from regeneration back to $NO_x$ removal. $NO_x$ removal agents that do not have a high heat of adsorption when switching from regeneration back to $NO_x$ removal are those that exhibit a total temperature rise across the NO removal agent (e.g., across the bed of $NO_x$ removal agent in a vessel) is ≤50° C., e.g., ≤20° C., such as ≤10° C.

(iv) The $NO_x$ removal agent is generally in the solid and/or liquid phase, and should not vaporize during regeneration. For example, the $NO_x$ removal agent optionally has an equilibrium vapor pressure ≤1 torr at 220° C.

(v) When at least a portion of the $NO_x$ removal agent is present in the form of a bed, e.g., in a packed bed within a vessel, the $NO_x$ removal agent should be of sufficient particle size such that the pressure drop (Δ P) across the bed is ≤2.0 bar (absolute), e.g., ≤1.5 bar, such as ≤1.0 bar.

(vi) The $NO_x$ removal agent should have a mechanical integrity such that Δ P does not increase during $NO_x$ removal by >0.1 times the Δ P at the start of $NO_x$ removal (e.g., the start of $NO_x$ removal in a Removal-Regeneration cycle). Optionally, the increase in Δ P during $NO_x$ removal is ≤0.1 times an initial Δ P at the start of $NO_x$ removal (generally ≤2.0 bar (absolute)).

(vii) The $NO_x$ removal agent should have a mechanical integrity such that fine attrition is ≤1 wt. % during $NO_x$ removal based on the weight of the $NO_x$ removal agent.

(viii) When the $NO_x$ removal agent is a $NO_x$ absorbent, the $NO_x$ removal agent should have a relatively high capacity for $NO_x$ absorption, e.g., ≥0.002%, such as ≥0.01%, or ≥0.10% on a weight basis (weight of absorbed $NO_x$ divided by weight of the absorbent, expressed as a percent).

Certain $NO_x$ removal agents are more selective for NO removal over $NO_2$ removal, and these can be used in aspects where, e.g., a significant amount of $NO_2$ is conducted away from a cold box before the first stream is exposed to a temperature where $NO_x$ can condense to form $NO_x$ gums or salts. For example, the first stream can be exposed to a $NO_x$ removal agent under conditions for removing remove ≥10.0 wt. % of the first stream's NO based on the weight of the first stream's NO and ≤1.0 wt. % of the first stream's $NO_2$ based on the weight of the first stream's $NO_2$. In some cases the $NO_x$ removal mechanism includes the conversion of NO to $NO_2$, the $NO_2$ can then be removed by adsorption utilizing one or more absorbents that are effective for removing $NO_2$ and/or (ii) conducting at least a portion of the $NO_2$ to one or more cold boxes, where the $NO_2$ can be removed by fractionation before reaching cold-temperature regions where $NO_x$ gums can form.

Certain aspects of the invention utilize one or more $NO_x$ removal agents that are capable of removing $NO_x$ from hydrocarbon containing streams, e.g., a first stream, wherein the first stream contacts the $NO_x$ removal agent at a space velocity (GHSV)≥$2.5 \times 10^4$ $hr^{-1}$, such as ≥$5.0 \times 10^4$ $hr^{-1}$.

Examples of suitable $NO_x$ removal agents include those comprising (i) one or more refractory (including refractory forms of carbon), e.g., one or more inorganic oxides, and optionally (ii) ≥1.0 wt. % of one or more elements selected from Groups 2-11 of the Periodic Table, based on the weight of the $NO_x$ removal agent, e.g., one or more metals selected from Groups 2, 6, 8, 10, or 11. Although the refractory can include oxides of one or more elements of Groups 13 or 14 of the Periodic Table (e.g., silica and/or alumina), the invention is not limited thereto. Accordingly, the refractory can comprise, e.g., one or more of beryllium oxide, zirconium oxide, magnesium oxide, or yttrium oxide. It is observed that when one or more Group 11 metal is used, relatively less metal is needed (on a weight basis) for a suitable $NO_x$ removal agent than is the case for metals of Groups 2, 6, 8, or 10. Suitable $NO_x$ removal agents include those capable of removing $NO_x$ from a hydrocarbon-containing stream at a GHSV≥$2.5 \times 10^4$ $hr^{-1}$, such as ≥$5.0 \times 10^4$ $hr^{-1}$. Accordingly, the $NO_x$ removal agent can include ≥5.0 wt. %, e.g., ≥10.0 wt. %, such as ≥15.0 wt. %, of a Group 11 metal. For example, the $NO_x$ removal agent can include ≥10.0 wt. % of Cu and/or Ag, e.g., ≥15.0 wt. % of Cu and/or Ag, such as 10.0 wt. % to 20.0 wt. % of Ag and/or Cu. Aspects of the process optionally utilize at least one $NO_x$ removal agent comprising aluminum oxide and ≥15.0 wt. % of Cu and/or Ag, based on the weight of the $NO_x$ removal agent. Although the term "metal" is used in describing the $NO_x$ removal agent, it is not meant to designate a particular chemical state for the elements of Groups 2-11 (e.g., one or more of Cu II, Cu I, or Cu 0), particularly when the $NO_x$ removal agent is in use for $NO_x$ removal from a hydrocarbon-containing stream. The metal can be included in a metal oxide, for example, but the invention is not limited $NO_x$ removal agents having at least one metal in the oxide form. Certain $NO_x$ removal agents will now be described in more detail. The invention is not limited to these $NO_x$ removal agents, and this description is not meant to foreclose the use of other $NO_x$ removal agents within the broader scope of the invention.

The $NO_x$ removal agent can comprise, e.g., adsorbent and/or redox material. Examples of suitable $NO_x$ removal agents include:

(a) Carbon, such as activated carbon or carbon fibers with or without modifications to enhance NO adsorption. Such materials are described, e.g., in Carbon, 1996, 34(8), 1027-1033 and Kenkyusho Hokoku, 1997, 10, 62-68). Conventional modifications can be utilized, but the invention is not limited thereto.

(b) $NO_x$ removal agents having modifications to enhance NO adsorption, including one or more of:

(i) Activated carbon impregnated with one or more metals selected from Groups 5 and 6 of the Periodic Table (as specified in the Periodic Chart of the Elements, The Merck Index, Merck and Co., 1996; the "Periodic Table"), including activated carbon impregnated with ≥1.0 wt. % (based on the weight of the activated carbon) of one or more of V, Mo, or W.

(ii) Carbon fibers treated with salt solutions, e.g., solutions containing one or more salts of one or more metals selected from Group 8 of the Periodic Table. Such salts are described, e.g., in Atmospheric Environment 1987, 21(9), 2053-2055. In certain embodiments, the salt solutions include ≥1.0 wt. % of at least one Fe salt, based on the weight of the salt solution.

(iii) Carbon surfaces treated with base metals, e.g., one or more metals selected from Groups 1 and 2 of the Periodic Table. Such materials are described in Separation Science and Technology 2002, 37(4) 937-956 and in Japanese Patent Application Publication No. JP07178316. Certain aspects utilize $NO_x$ removal agent which include ≥0.1 wt. % of potassium based on the weight of the $NO_x$ removal agent.

(c) Redox materials, including those comprising one or more metal oxide, e.g., a redox material including ≥1.0 wt. % (based on the weight of the redox material) of one or more oxides of Groups 5, 6, 7, 8, 9, and 11 metals of the Periodic Table. Such oxides include, e.g., one or more oxides of Co, Cu, Fe, Mn, V, or Cr. Suitable redox materials include conventional redox materials supported on oxides. Conventional redox materials and operating conditions can be utilized, but the invention is not limited thereto. Conventional redox materials and operating conditions are described, e.g., in the Journal of Materials Science, 2008 43(19), 6505-6512; Studies in Surface Science and Catalysis 2006, 159, 229-232; Langmuir 2001, 17, 4997; and in German Patent Application Publication No. DE4012982A1, which is incorporated by reference herein in its entirety. Certain aspects utilize materials comprising ≥10.0 wt. % of one or more of Cu, Ag, or Au, e.g., ≥15.0 wt. % of Cu based on the weight of the redox material.

(d) Layered materials (e.g. hydrotalcites). Suitable layered materials include those having one or more metals in the interlayer, such as Co(II) or Fe(II) in the interlayer. Certain aspects utilize $NO_x$ removal agents which include $CeO_2$—$Al_2O_3$, described in Appl. Cat B: Env. 2009, 88(1-2), 113-126, which removes NO by reacting it with CO to produce surface NCO on the surface of the $NO_x$ removal agent.

(e) Metal sulfides, including, e.g., layered metal sulfides, and in particular including metal sulfides such as those utilized as hydroprocessing-type catalysts. Certain aspects utilize $NO_x$ removal agents which include one or more metal sulfides that show high affinity towards NO adsorption e.g. $NO_x$ removal agents comprising ≥1.0 wt. % (based on the weight of the removal agent) of one or more of $MoS_2$, NiMo, or CoMo). Such materials are described, e.g., in J. CHEM. SOC. FARADAY TRANS., 1995, 91(3), 517-524; and Applied Catalysis A: General, 197 (1), 2000, 69-78.

(f) Ordered mesoporous and microporous materials, such as one or more aluminophosphates and/or one or more zeolites. Certain aspects utilize $NO_x$ removal agents which include ≥1.0 wt. % (based on the weight of the $NO_x$ removal agent) of one or more of:

(i) One or more composites of 13X-Alumina, such as those described in European Patent Applicant Publication No. EP862938.

(ii) One or more metal-exchanged zeolites, such as those described in Japanese Patent Application Publication No. JP08299756A; Huanjing Huaxue, 1996, 15(4), 289-295; Transactions of the Materials Research Society of Japan, 1994, 18A, 401-404. The metal can be, e.g., at least one metal selected from Group 11 of the Periodic Table. In certain embodiments, the $NO_x$ removal agent comprises ≥1.0 wt. % (based on the weight of the NO removal agent) of ZSM-5 and/or Zeolite Y that has been Ag-exchanged and/or Cu-exchanged.

(iii) Metal-exchanged aluminophosphates, e.g., one or more aluminophosphates exchanged with one or more metals selected from Group 9 of the Periodic Table. Such metal-exchanged aluminophosphates are described, e.g., in Catalysis Today (1999) 54(4) 547-552. Certain aspects utilize $NO_x$ removal agent which include ≥1.0 wt. % of CoAPO-5 based on the weight of the $NO_x$ removal agent.

(g) Combinations of (a)-(f).

Regeneration

Certain $NO_x$ removal agents have a limited capacity for removing $NO_x$, and when this capacity is exceeded the ability of the removal agent to further remove $NO_x$ is diminished. This condition can be overcome, e.g., the removal agent's ability to remove $NO_x$ can be at least partially restored, by regenerating the $NO_x$ removal agent. Although conventional regeneration methods can be utilized, such as exposing the removal agent to an elevated temperature, optionally in the presence of a sweep gas, the invention is not limited thereto.

When the $NO_x$ removal agent includes at least one absorbent, regeneration can be achieved, e.g., by flowing a heated gas over the $NO_x$ removal agent. Optionally, the regeneration is conducted at a pressure that is less than the operating pressure utilized during $NO_x$ removal. For example, in certain embodiments the regeneration is performed at a pressure that is ≤10 bar (absolute), e.g., in the range of from 3 bar (absolute) to 7 bar (absolute). During regeneration, the $NO_x$ removal agent is generally exposed to a temperature ≥120° C., e.g., ≥177° C., such as ≥200° C. This can be accomplished, e.g., by exposing the $NO_x$ removal agent to a heated vapor or gas ("heated gas"). Preferably the gas is an $O_2$ and/or $H_2$ containing gas, such as a gas that comprises ≥1.0 wt. % of one or more of molecular oxygen or molecular hydrogen. In certain embodiments, the gas comprises tail gas.

Optionally, the flow direction of the regeneration gas is countercurrent to the flow of the first stream. For example, for at least a portion of the regeneration interval, such as for substantially all of the regeneration interval, the regeneration gas flow direction is opposite that of the first stream during $NO_x$ removal. In other aspects, the flow direction of regeneration gas during removal-agent regeneration is in the same direction as that of the first stream during $NO_x$ removal. Optionally, $NO_x$ removal agent regeneration is conducted for a regeneration time interval (a second time interval) that is ≥0.01 hours, or ≥0.1 hours, or ≥1.0 hours, but ≤10,000 hours, or ≤1000 hours, or ≤100 hours. In certain embodiments, the time interval is in the range of from 5 hours to 500 hours, or 20 hours to 500 hours, e.g., 50 to 200 hours, such as 70 to 150 hours, or 80 to 100 hours. For example, the time interval can be in the range of from 10 hours to 200 hours, such as 15 hours to 100 hours, or 20 hours to 60 hours.

In aspects where at least a portion of the $NO_x$ removal agent comprises one or more redox agents, regeneration can be achieved by exposing the redox agent to molecular oxygen and/or molecular hydrogen under suitable regeneration conditions. Conventional redox agent regeneration, such as when the redox agent is exposed to a gas containing molecular oxygen or a gas containing molecular hydrogen can be utilized, but the invention is not limited thereto. Optionally, the $NO_x$ removal agent comprises ≥5.0 wt. % of at least one redox agent (e.g., ≥10.0 wt. %), wherein the regeneration conditions include a regeneration temperature in the range of 175.0° C. to 235.0° C., at a pressure in the range of 3 bar (absolute) to 7 bar (absolute), for a time ≤100 hours, at a WHSV in the range of 1 $hr^{-1}$ to 100 $hr^{-1}$, e.g., 2 $hr^{-1}$ to 50 $hr^{-1}$, such as 3 $hr^{-1}$ to 50 $hr^{-1}$, or 4 $hr^{-1}$ to 25 $hr^{-1}$. The regenerating gas can comprise, e.g., ≥1.0 wt. % of molecular hydrogen or molecular oxygen, the weight percents being based on the weight of the regeneration gas.

Certain aspects utilize a $NO_x$ removal agent which comprises ≥25.0 wt. % of at least one $NO_x$ adsorbent based on the weight of the $NO_x$ removal agent (e.g., ≥90.0 wt. %). In these aspects, the regeneration conditions can include, e.g., a regeneration temperature in the range of 175.0° C. to 235.0° C., at a pressure in the range of 3 bar (absolute) to 7 bar (absolute), for a time in the range of 50 to 200 hours, at a WHSV in the range of 1 $hr^{-1}$ to 100 $hr^{-1}$. The regenerating gas can comprise ≥90.0 wt. % of tail gas, based on the weight of the regenerating gas.

When a vessel containing one or more $NO_x$ removal agents is operated in parallel with at least a second vessel, the second vessel also containing one or more $NO_x$ removal agents, it can be desirable to provide means for operating the first vessel or vessels in $NO_x$-removal mode and the second vessel or vessels (after the second vessel has been utilized for removing $NO_x$) in regeneration mode. In other words, the process can be operated cyclically, e.g., where the removal agents of one vessel remove $NO_x$ from the cold box's feed stream and the removal agents of the other vessel are being regenerated. Valve means can be utilized to do this, including conventional valve means, but the invention is not limited thereto. Upgraded first stream conducted away from the first and second vessels can be combined, e.g., for further processing.

Cycles can be continuous, semi-continuous, or some combination thereof. Cycles can be periodic, and of substantially equal time duration, but this is not required. The $NO_x$ removal portion of the cycle (first interval) can be of the same time duration as for the regeneration portion of the cycle (second interval), but this is not required. During cyclic operation, the duration of the first interval can be, e.g., ≥0.01 hours, or ≥0.1 hours, or ≥1.0 hours, but ≤10,000 hours, or ≤1000 hours. Optionally, the duration of the first interval is in the range of from 50 to 250 hours, e.g., 75 hours to 125 hours, or 80 to 100 hours. The duration of the second interval can be, e.g., ≥0.01 hours, or ≥0.1 hours, or ≥1.0 hours, but ≤10,000 hours, or ≤1000 hours, or ≤100 hours. In certain aspects, the duration of the second interval is in the range of from 20 hours to 500 hours, e.g., 50 to 200 hours, such as 70 to 150 hours, or 80 to 100 hours. Optionally, there is a time between the first and second intervals when the $NO_x$ removal agent is not exposed to the first stream and is not exposed to the regeneration gas. This is referred to as "idle mode", which can occur, e.g., during the actuation of valves controlling the flow of process gasses. It is generally desirable for the duration of idle mode to be short, e.g., ≤1.0 hour. Optionally, the first and second intervals are non-overlapping time intervals.

Utilizing a $NO_x$ Removal Agent and a Water Removal Agent

The $NO_x$ removal agent can be utilized with at least one water removal agent (a drying agent). It is conventional to utilize at least one water removal agent, e.g., for removing water from process streams, e.g., process streams which comprise hydrocarbon. Generally, when the first stream comprises water, at least one water removal agent is located in a vessel (e.g., a drier), the vessel and its water removal agent being operated under conditions that are effective for removing at least a portion of the first stream's water, e.g., ≥50.0 wt. % of the first stream's water based on the weight of the first stream's water, such as ≥90.0 wt. %. Conventional water removal agents and conventional water removal process conditions can be utilized, but the invention is not limited thereto. For example, the water removal agent can comprise ≥90.0 wt. % of molecular sieve type 3A, based on the weight of the water removal agent.

In certain aspects, at least one water removal agent is utilized with at least one $NO_x$ removal agent in for removing water and $NO_x$ from the first stream. Optionally, at least a portion of the $NO_x$ removal agent is located in at least one $NO_x$ removal region, the $NO_x$ removal region being upstream and/or downstream of a water removal region. For example, at least a portion of the $NO_x$ removal agent can be located in at least one first bed within a drier, with at least a portion of the water removal agent being located in at least a second bed within the drier. In other words, the drier can contain at least one bed of a $NO_x$ removal agent (a first removal agent) and at least one bed of a water removal agent (a second removal agent), wherein (i) ≥90.0% (wt. basis) of the second removal agent is located upstream of ≥90.0% (wt. basis) of the first removal agent, and (ii) upstream is with respect to the flow of the first stream during $NO_x$ removal. For example, in a vessel containing two beds, substantially all of the water removal agent in the vessel can be located in a bed that is upstream of a second bed, the second bed containing substantially all of the $NO_x$ removal agent in the vessel. The first removal agent can comprise ≥90.0 wt. % of at least one solid absorbent and/or at least one redox material and (ii) the second removal agent can comprise ≥90.0 wt. % of a second solid absorbent. Optionally, the $NO_x$ removal agent and the water removal agent are each selective for their intended purpose, e.g., the second removal agent removes ≤1.0 wt. % of the first stream's $NO_x$, based on the weight of the first stream's $NO_x$, and the first removal agent removes ≤1.0 wt. % of the first stream's water based on the weight of the first stream's water. Optionally, the first removal agent has a bulk density within about +/−20.0% (weight basis) of the second removal agent's bulk density, e.g., within about +/−15.0%; and (i) ≥50.0 wt. % of the first stream's $NO_x$ can be removed and (ii) a space velocity (GHSV)≥2.5×$10^4$ $hr^{-1}$ maintained. Optionally, the drier contains 0.1 wt. % to 49.0 wt. % of the first removal agent and 51.0 wt. % to 99.9 wt. % of the second removal agent, the weight percents being based on the combined weight of the first and second removal agents in the drier. For example, the drier can contain 1.0 wt. % to 15.0 wt. % of the first removal agent and 85.0 wt. % to 99.0 wt. % of the second removal agent, such as 5.0 wt. % to 10.0 wt. % of the first removal agent and 90.0 wt. % to 95.0 wt. % of the second removal agent; the first removal agent having a bulk density within about +/−10.0% of that of the second removal agent.

When at least one $NO_x$ removal agent is utilized together with at least one water removal agent, it can be efficient to regenerate the water removal agent and the $NO_x$ removal agent during the same time interval. For example, in embodiments where the $NO_x$ removal agent and the water removal agent occupy beds in a vessel, the vessel can be operated under conditions which are sufficient for at least partially regenerating the $NO_x$ removal agent and at least partially regenerating the water removal agent during a regeneration time interval.

When at least a portion of the $NO_x$ removal agent is located in a first vessel and at least a portion of the water removal agent is located in a second vessel, the first and second vessels can each be operated under conditions which are sufficient for at least partially regenerating the $NO_x$ removal agent and at least partially regenerating the water removal agent during a regeneration time interval. In these aspects, the time duration for regeneration of the $NO_x$ removal agent can be the same as the time duration for regeneration of the water removal agent, but this is not required. For example, different regeneration time durations can be utilized when the desired amount of water removal agent regeneration can be achieved in less time than is needed to achieve the desired amount of the $NO_x$ removal agent regeneration. Generally, the first time duration (the time duration for regeneration of the $NO_x$ removal agent in the first vessel) and the second time duration (for regeneration of the water removal agent in the second vessel) each occur during the regeneration interval.

In certain aspects, the first removal agent (the $NO_x$ removal agent) is located in a first vessel, and the second removal agent (the water removal agent) is located in a second vessel, the second vessel being, e.g., upstream of the first vessel with respect to the flow of the first stream. Optionally, third and fourth vessels are utilized, the third vessel containing a third removal agent (a $NO_x$ removal agent) and the fourth vessel containing a fourth removal agent (a water removal agent). The fourth vessel can be located upstream of the third vessel, with upstream being with respect to the flow of the first stream. In other words, the first and second vessels are in series, as are the third and fourth vessels. The series combination of the first and second vessels is operated in parallel with the series combination of the third and fourth vessels, utilizing, e.g., valve means. Upgraded first stream conducted away from vessels 1-4 can be combined, e.g., for further processing. During the first time interval, the first and second vessels are in $NO_x$/water-removal mode, and the third and fourth vessels are in regeneration mode. During the second time interval, the first and second vessels are in regeneration mode, and the third and fourth vessels are in $NO_x$/water-removal mode. Operating conditions, interval durations, removal agent type and amounts can be, e.g., the same as those disclosed in the preceding embodiments.

Since in these aspects the water removal agent and $NO_x$ removal agent are not located in the same vessel, the duration of $NO_x$ removal within the first interval ($t_1$) can be the same as or different from the duration of water removal during the first interval ($t_2$), e.g., by utilizing one or more by-pass valves to route at least a portion of the first stream around the first or second vessel as the case may be. During the second interval, the removal agents of the first and second vessels are regenerated. The duration of regeneration of the first vessel can be the same as or different from that of the second vessel. Also during the second interval, the third and fourth vessels are operated in $NO_x$/water-removal mode. As is the case for the first and second vessels, the duration of $NO_x$ removal within the second interval ($t_3$) can be the same as or different from the duration of water removal during the second interval ($t_4$). Optionally, the first and second intervals are non-overlapping intervals. Optionally, $t_2$ is in the range of $t_1 \cdot 0.75$ to $t_1 \cdot 1.25$ and $t_4$ is in the range of $t_3 \cdot 0.75$ to $t_3 \cdot 1.25$. Optionally ≥90.0% (wt. basis) of the second removal agent is located upstream of ≥90.0% (wt. basis) of the first removal agent and (ii) ≥90.0% (wt. basis) of the fourth removal agent is located upstream of ≥90.0% (wt. basis) of the third removal agent. For example, substantially all of (i) the first and (ii) the second removal agents are located in a first vessel, substantially all of (ii) the third and (iii) the fourth removal agents are located in a second vessel, where the term "substantially all" is meant to exclude fines which can escape the process. Optionally, (i) the first stream contacts the first removal agent at a space velocity (GHSV)≥$5.0\times10^4$ $hr^{-1}$ and $t_2$ is in the range of $t_1 \cdot 0.9$ to $t_1 \cdot 1.1$, (ii) the first stream contacts the third removal agent at a space velocity (GHSV)≥$5.0\times10^4$ $hr^{-1}$ and $t_4$ is in the range of $t_3 \cdot 0.9$ to $t_3 \cdot 1.1$, (iii) the first and second time intervals are each ≤100 hours; (iv) the first and third removal agents comprise a first adsorbent and the second and fourth removal agents comprise a second adsorbent; or (v) the first adsorbent has a NOx adsorbent capacity ≥0.11% (weight basis) during at least one of $t_1$ or $t_3$. The second adsorbent can be a drier, for example.

Removing $NO_x$ from a Pyrolysis Stream

At least a portion of the first stream can be derived from one or more pyrolysis process. Aspects of the invention as they may apply to one such pyrolysis process, steam cracking, will now be described in more detail. The invention is not limited to the processing of first streams derived from steam cracking, and the following description is not meant to foreclose the use of first streams derived all or in part from other processes or sources.

A steam cracker utilizes thermal pyrolysis to convert hydrocarbon feeds and feed mixtures (e.g., hydrocarbons boiling in the range of ethane's atmospheric boiling point to that of heavy oil) to produce higher-value products. The product of the pyrolysis can include, e.g., olefins such as ethylene and propylene. Besides olefin, the pyrolysis product generally comprises molecular hydrogen and methane. At least a portion of the product of the hydrocarbon pyrolysis is generally conducted away from the steam cracker as an outlet stream. Generally, the outlet stream is cooled (e.g., in one or more heat exchanger stages, such as transfer line heat exchangers) and then conducted to at least one compression stage, e.g., one have multi-stage compression and inter-stage cooling. The compression stage increases the outlet stream's pressure from an initial pressure near ambient pressure (about 1.0 bar, absolute) to an outlet pressure that is generally ≥14 bar (absolute), e.g., in the range of 15 bar to 45 bar. Sufficient compression and cooling is utilized to allow the separation from the outlet stream of ≥50.0 wt. % of the outlet stream's $C_{4+}$ hydrocarbons, based on the weight of the outlet stream's $C_{4+}$ hydrocarbons, such as ≥75.0 wt. %, or ≥90.0 wt. %, to produce an upgraded outlet stream.

Following the separation of at least a portion of the outlet stream's $C_{4+}$ hydrocarbons, the upgraded outlet stream is then typically treated to remove at least a portion of the upgraded outlet mixture's acidic compounds (generally one or more acid gases, e.g., $CO_2$ and sulfur compounds such as $H_2S$, COS, $SO_2$, $SO_3$) to produce a first stream, e.g., the first stream (or first mixture) as specified in the preceding embodiments. Aspects of the invention include those directed towards removing $NO_x$ and optionally water from a first stream that is derived at least in part from steam cracking, as illustrated in FIG. 3.

Figure 3:
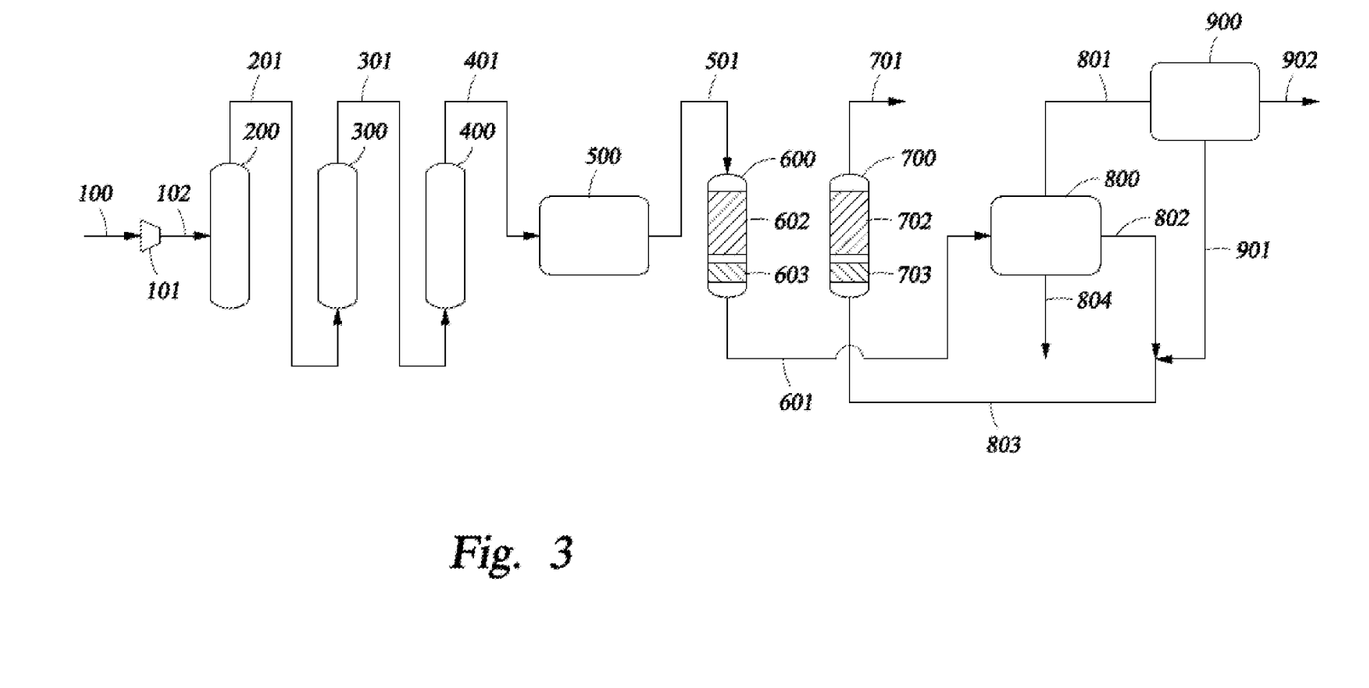
FIG. 3 schematically shows an embodiment of the invention including a gas treatment stage upstream of a methane-molecular hydrogen separation stage.

As shown schematically in FIG. 3, a steam cracker's outlet stream 100 is conducted to compression stage 101, and the compressed stream is then conducted via line 102 to separation stage 200. Separation stage 200 can include one or more fractionators, knock-out drums, etc., and is utilized for separating at least a portion of the compressed outlet stream's $C_{4+}$ compounds. An upgraded outlet stream, comprising, e.g., molecular hydrogen, water, methane, ethylene, ethane, carbon monoxide, carbon dioxide, and $NO_x$, is conducted away from separation stage 200 via line 201 to acid gas-removal stage 300, for removing from the upgraded outlet stream at least a portion of any $CO_2$, $H_2S$, COS, $SO_2$, $SO_3$, etc. Conventional processes can be utilized for removing the acid gases, including processes utilizing caustic or one or more amines, but the invention is not limited thereto. When caustic amine is utilized, line 301 can be utilized to conduct the upgraded outlet stream from acid gas removal stage 300 to aqueous-wash stage 400, where water is utilized for removing at least a portion of any caustic or amine from the upgraded outlet stream.

Selective hydrogenation can be utilized for converting at least a portion of any acetylene, methyl acetylene, propadiene, butadiene, etc. in the upgraded outlet stream to monoolefins or paraffins. For example, in certain embodiments where the outlet stream contains acetylene, one or more acetylene converters can be utilized to convert at least a portion of any acetylene in the upgraded outlet stream to, e.g., ethylene. Conventional acetylene conversion processes can be used, e.g., front end and/or back end acetylene conversion processes, but the invention is not limited thereto. For example, acetylene conversion conditions can include exposing the upgraded outlet stream to catalytic hydrogenation conditions in the presence of a catalytically effective amount of at least one acetylene conversion catalyst comprising ≥1.0 wt. % based on the weight of the catalyst of at least one element selected from Groups 1, 2, 8, 9, 10, and/or 12, of the Periodic Table.

As shown in FIG. 3, line 401 can conduct the upgraded outlet stream via line 401 to a front-end acetylene conversion stage 500. A first stream containing ≥1.0 wt. % methane, ≥1.0 wt. % molecular hydrogen, ≥2.0 ppbw $NO_x$, based on the weight of the first stream and ≥0.05 mole % of water per mole of the first stream, is conducted away from the acetylene conversion stage 500 via conduit 501.

Processes represented by FIG. 3 utilize at least two vessels for removing water and $NO_x$ from the first stream, vessels 600 and 700. These vessels each contain at least two beds, an upstream bed (upstream being with respect to the flow of the first stream) comprising at least one water removal agent and a downstream bed comprising at least one $NO_x$ removal agent. The water removal agents and the $NO_x$ removal agents can be the same as those specified in the preceding embodiments. Optionally, vessels 600 and 700 contain substantially the same types of $NO_x$ and/or water removal agents, substantially the same amounts of these agents, substantially the same bed locations, and are operated under substantially the same process conditions. Valve means (not shown) can be utilized for (i) lessening or diverting the first stream's flow away from vessel 600 (to switch from $NO_x$ removal mode to an idle mode or a regeneration mode), and (ii) to re-direct of increase the first stream's flow to vessel 700 (to switch vessel 700 away from regeneration mode to an idle mode or $NO_x$ removal mode). Switching can be configured so that the process operates continuously, with (i) vessel 600 in $NO_x$ removal mode and vessel 700 in regeneration mode during a first time interval, and (ii) vessel 600 in regeneration mode and vessel 700 in $NO_x$ removal mode during a second time interval. Optionally, one or more of the vessels is in idle mode during a third interval, the third interval being between the first and second intervals. The first and second intervals (and optional third interval) can be operated cyclically in sequence, one interval after the other, so that the upgrading can be done continuously or semi-continuously. The first and second intervals can be of substantially equal length, but this is not required.

The first stream can have a water content ≥0.05 mole % per mole of the first stream and a $NO_x$ content ≥100 ppbw based on the weight of the first stream. Under these conditions, vessels 600 and 700 can each contain a $NO_x$ removal agent and a water removal agent, the $NO_x$ removal agent and the water removal agent each being selected from one or more of those described in the preceding embodiments. The water removal agent of vessel 600 is located in bed 602, with the $NO_x$ removal agent being located in bed 603. Bed density is (i) substantially the same in beds 602 and 603, and (ii) in the range of 1.50 g/cm$^3$ to 2.0 g/cm$^3$. Bed 602 contains a water removal agent, e.g., molecular sieve type 3A. Bed 603 contains a $NO_x$ removal agent having a capacity ≥0.02% (weight basis), such as ≥0.03%, or even ≥0.10%, e.g., metal-oxide supported, hydroprocessing-type catalyst containing nickel and molybdenum. Vessel 600 contains 5.0 wt. % to 10.0 wt. % of the $NO_x$ removal agent (the hydroprocessing catalyst, located in bed 603) and 90.0 wt. % to 95.0 wt. % of the water removal agent (molecular sieve type 3A, located in bed 602), the weight percents being based on the combined weight of the $NO_x$ removal agent and the water removal agent. Vessel 700 is substantially the same as vessel 600, with beds 702 and 703 containing the substantially the same materials and being of substantially the same bed density as that of vessel 600. The time duration of the second interval can be, e.g., within about +/−10% relative to that of the first time interval, such as when the first and second time interval are of substantially equal duration. The invention is not limited to these processes, and the description of these processes with respect to FIG. 3 is not meant to foreclose other processes within the broader scope of the invention, such as those where the vessels do not contain the same types or amounts of the removal agents.

Continuing with reference to FIG. 3, vessel 600 is in $NO_x$ removal mode and vessel 700 is in regeneration mode (i.e., during the first time interval). Process conditions for vessel 600 include a pressure in the range of 15 bar to 40 bar (absolute) and a temperature in the range of 4.0° C. to 50.0° C. The space velocity (GHSV) in bed 603 is ≥2.5×10$^4$ hr$^{-1}$, such as ≥5.0×10$^4$ hr$^{-1}$; and the space velocity (GHSV) in bed 602 is ≥2.0×10$^3$ hr$^4$. When the first stream is exposed to the first and second beds in vessel 600 under these conditions, (i) the first removal agent removes ≥50.0 wt. % of the first stream's $NO_x$, based on the weight of the stream's $NO_x$, and (ii) the second removal agent removes ≥50.0 wt. % of the first stream's water, based on the weight of the first stream's water. Accordingly, an upgraded first stream is produced, the upgraded first stream being conducted away from vessel 600 via line 601 to a stage 800. At least a portion of the upgraded first stream's molecular hydrogen is separated in stage 800 and conducted away from stage 800 via line 801. Stage 800 can comprise, e.g., one or more cold boxes. At least a portion of the $C_{2+}$ hydrocarbons in the upgraded first stream are conducted away via line 804. The process can further comprising polymerizing at least a portion of the $C_{2+}$ hydrocarbons in one or more stages (not shown) downstream of stage 800. A tail gas comprising, e.g., methane, is conducted away from stage 800 via line 802. The molecular hydrogen is optionally purified in purification stage 900, with the purified molecular hydrogen being conducted away via line 902. By-products of the purification, e.g., methane, can be conducted away from the purification stage via line 901, and optionally combined with the tail gas.

At least a portion of the tail gas is conducted via line 803 to vessel 700 for regenerating the removal agents of beds 702 and 703. Regeneration conditions include, e.g., a pressure in the range of 1 bar to 10 bar (absolute), such as 4 bar to 8 bar (absolute), and a temperature in the range of 100° C. to 400° C., such as 175° C. to 230° C. The products of the regeneration are conducted away via line 701.

At the end of the first interval, valve means (not shown) can be utilized for switching vessel 600 to regeneration mode and vessel 700 to $NO_x$ removal mode during a second time interval. The duration of the first interval can be selected so as to maintain the amount of water in the upgraded first stream to ≤1 ppmw and the $NO_x$ amount to <5 ppbw, e.g., <3 ppbw, such as ≤2.0 ppbw, or even ≤1.0 ppbw, the weight percents being based on the weight of the upgraded first stream. When the first interval is selected this way, ≥5 ppbw NO$_x$ is removed from the first stream, based on the weight of the first stream, e.g., ≥20.0 ppmw NO$_x$, such as ≥100.0 ppbw NO$_x$, or ≥200.0 ppbw NO$_x$, or ≥300 ppbw NO$_x$ is removed. In such cases, the upgraded first stream generally comprises ≤100 ppbw NO$_x$ based on the weight of the upgraded first stream, e.g., <5 ppbw, such as <3 ppbw, or even lower, such as ≤2.0 ppbw, or even ≤1.0 ppbw.

Optionally, the first and second intervals are each in the range of about 50 to about 150 hours, e.g., 80 hours to 100 hours.

Certain aspects of the invention represent an improvement to a process for removing water from a stream comprising water, NO$_x$, methane, and molecular hydrogen, and optionally C$_2$ hydrocarbon. It is observed that ≥5 ppbw of the first stream's NO$_x$ is removed without significantly lessening the amount of water removed from the first stream by substituting one or more of the NO$_x$ removal agents of the preceding embodiments for at least a portion of the water removal agent, e.g., a minor amount of the water removal agent, such as ≤15.0 wt. % of the water removal agent based on the weight of the water removal agent. For example, one conventional process has two water removal vessels in cyclic operation, with first and second intervals each in the range of 50 to 150 hours. The vessels each contain substantially the same type and amount of water removal agent, e.g., type 3A molecular sieve. In such an embodiment, ≥1.0 wt. % of the water removal agent (based on the weight of the water removal agent) can be replaced with a substantially equivalent amount (and optionally substantially equivalent bed density) of at least one NO$_x$ removal agent having a capacity ≥0.002%. Other process conditions can remain substantially the same as they were before the substitution of the NO$_x$ removal agent for a portion of the water removal agent, such as (i) the feed rate of the upgraded first stream to the vessel in NO$_x$-removal and water-removal mode, (ii) the temperature and pressure in the vessel in NO$_x$-removal and water-removal mode, (iii) regeneration gas type and feed rate to the vessel in regeneration mode, and (iv) regeneration temperature and pressure.

Optionally, the amount or water removal agent that is replaced with NO$_x$ removal agent is in the range of about 1 wt. % to about 15 wt. %, e.g., about 5 wt. % to about 10 wt. %. Replacing ≤15.0 wt. % of the water removal agent, e.g., ≤10.0 wt. % of the water removal agent with a NO$_x$ removal agent will slightly decrease the duration of the first and second intervals (e.g., a decrease of ≤15% of the original time intervals), in order to maintain the amount of water in the upgraded first stream at an amount ≤1 ppmw based on the weight of the upgraded first stream.

Further Processing

Optionally, the upgraded first stream is conducted to a separation stage, e.g., for separating and conducting away (i) at least a portion of the first stream's molecular hydrogen and (ii) at least a portion of the first stream's methane. Referring again to FIG. 3, the upgraded first stream is optionally conducted away from vessel 600 via line 601 to separation stage 800. Means can be provided (not shown) for combining the portion of the upgraded first stream that is conducted away from vessel 600 with the portion conducted away from vessel 700, so that the process can operate continuously or semi-continuously. Stage 800 can include one or more cold boxes, such as the cold box illustrated schematically in FIG. 4.

Figure 4:
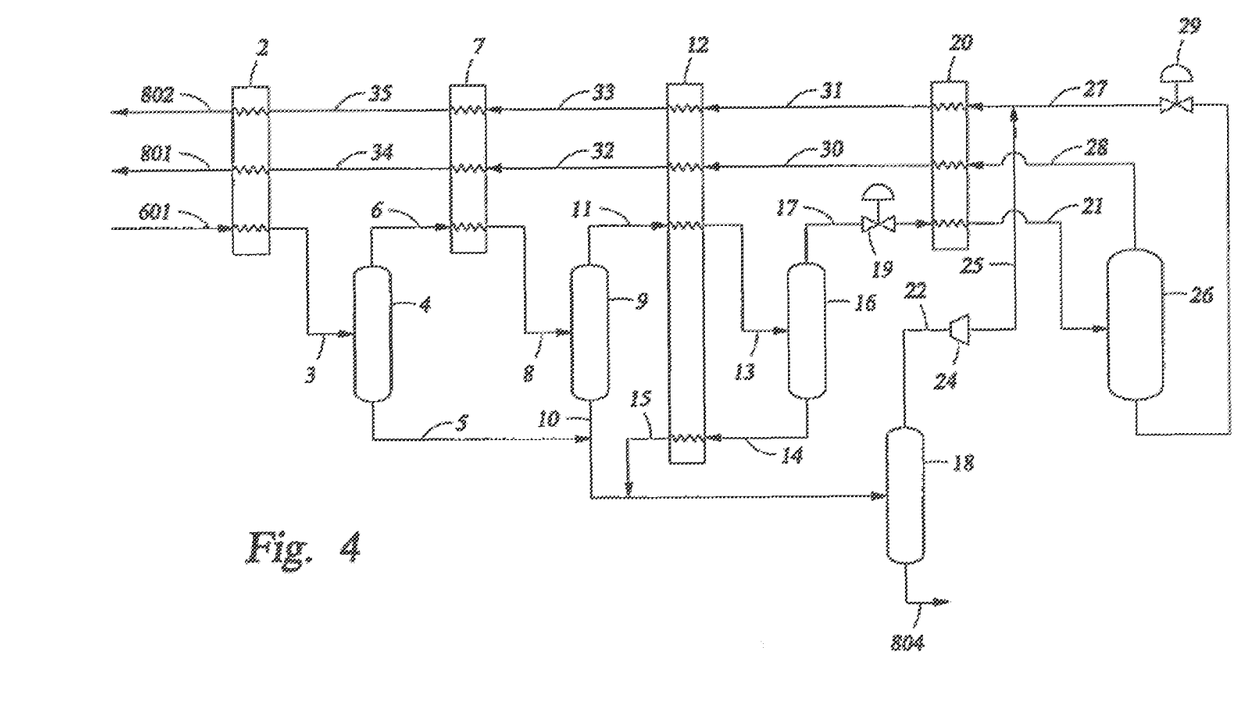
FIG. 4 schematically illustrates the use of a cold box for removing methane and molecular hydrogen from a hydrocarbon-containing feed stream.

As shown in FIG. 4, the upgraded first stream (which can be vapor phase or mixed vapor-liquid phase) is conducted to a first heat exchanger 2 where the upgraded first stream is cooled by exposing the upgraded first stream to a reduced temperature provided by at least a portion of the cold box effluent 34 and 35. The upgraded first stream (now cooled) is conducted away from heat exchanger 2 via line 3 to drum 4, wherein a condensed liquid portion of the first stream is conducted away via line 5 and a vapor phase is conducted away via line 6. The vapor phase is cooled in heat exchanger 7 by exposing the vapor phase to a reduced temperature in heat exchanger 7, the reduced temperature being provided by cold box effluent 32 and 33. The vapor phase is conducted away from heat exchanger 7 via line 8 to second drum 9, wherein a second liquid condensed liquid phase is conducted away via line 10 and a second vapor phase is conducted away via line 11. The second vapor phase is cooled in heat exchanger 12 by exposing the second vapor phase to a reduced temperature in heat exchanger 12, the reduced temperature being provided by cold box effluent 30 and 31.

The second vapor phase is conducted away from heat exchanger 12 via line 13 to third drum 16, wherein a third condensed liquid phase is conducted away via line 14 and a third vapor phase is conducted away via line 17.

The third vapor phase, which comprises primarily molecular hydrogen and methane is then conducted through valve 19 to heat exchanger 20, where the third vapor phase is exposed to a reduced temperature provided by cold box effluent 27 and 28. The third vapor phase is conducted away from heat exchanger 20 to drum 26, which is utilized for separating condensed methane and vapor molecular hydrogen from the third vapor phase. A second stream (a methane-rich stream, generally in the liquid phase) is conducted away from drum 26 via line 27 to valve 29 where the pressure is reduced to provide refrigeration, and then via lines 31, 33, and 35, through heat exchangers 20, 12, 7, and 2, to line 802. A third stream (a molecular hydrogen-rich stream, generally in the vapor phase) is conducted away from drum 26 via line 28, and then via lines 30, 32, and 34, through heat exchangers 20, 12, 7, and 2, to line 801.

In certain embodiments, the third liquid phase is conducted through heat exchanger 12, and then away from heat exchanger 12 via line 15 to be combined with the first and second liquid phases. Optionally, the combined liquid phases are conducted to drum 18, for separating a fourth liquid phase and a fourth liquid phase and a fourth vapor phase. When the first stream is derived from a steam cracker outlet stream, the fourth liquid phase comprises primarily C$_2$ hydrocarbon, which is conducted away via line 804. Olefin in the C$_2$ hydrocarbon, such as ethylene and/or propylene, can be polymerized if desired. The fourth vapor stream, comprising primarily methane, is conducted away via line 22, liquefied in stage 24 (e.g., a turbo expander), and then combined with the methane of line 27 downstream of valve 29.

The successive condensations effected by heat exchangers 2, 7, 12, and 20 and drums 4, 9, 16, and 26 generally result in exposing portions of the upgraded first stream to progressively lower temperatures, e.g., ≤0° C. in heat exchanger 2, ≤−50° C. in heat exchanger 7, ≤−75° C. in heat exchanger 12, and ≤−100° C. in heat exchanger 20, such as ≤−140.0° C. or even ≤−160.0° C. Pressure can be, e.g., ≥1.0 bar (absolute), such as in the range of from 10.0 bar (absolute) to 35.0 bar (absolute). It has been observed that when the amount of NO$_x$ in the upgraded first stream is not maintained at an amount that is ≤5 ppbw based on the weight of the upgraded first stream, that NO$_x$ gums and salts undesirably accumulate in the cold box of FIG. 4 primarily in the following locations: proximate to heat exchanger 12 at lines 15 and 14, proximate to heat exchanger 20 at lines 27 and 31, and proximate to drum 26 at line 27. One aspect of the invention overcomes this difficulty by maintaining the amount of $NO_x$ in the upgraded first stream at an amount that is <5 ppbw or <3 ppbw, or even lower, such as ≤2.0 ppbw, or even ≤1.0 ppbw.

EXAMPLES

In the following numerical simulations (Examples 1 and 2), a first stream is provided, the first stream having a molecular weight of 21.25 grams per mole and comprising 32.26 mole % of molecular hydrogen, 16.52 mole % of methane, 24.38 mole % of ethylene, 13.75 mole % of ethane, 4.50 mole % of propylene, 1.5 mole % of butadiene, and 5.59 mole % of $C_{3+}$ saturated hydrocarbon, the mole percents being based on one mole of the first stream. The first stream further comprises 1.0 wt. % of water and 300 ppbw of $NO_x$, based on the weight of the first stream.

Example 1

First and second beds are provided, the first bed comprising a water removal agent and the second bed comprising a $NO_x$ removal agent. The $NO_x$ removal agent has a capacity of 0.11%. Each bed has a bed density of 1.85 g/cm$^3$. The first bed is upstream of the second bed with respect to the flow of the first stream. The $NO_x$ removal agent comprises 5.0 wt. % of the combined weight of the $NO_x$ removal and water removal agents, the water removal agent comprises 95.0 wt. %.

The first stream is exposed to the first bed and second bed under the following conditions to produce an upgraded second mixture: a temperature of 25.0° C., a pressure of 20 bar (absolute), a water removal agent space velocity (GHSV) 3,575 hr$^{-1}$, and a $NO_x$ removal agent space velocity (GHSV) of 71,504 hr$^{-1}$.

In this simulation, the upgraded first stream contains ≤1 ppmw of water and ≤1 ppbw (essentially an undetectable amount) of $NO_x$, based on the weight of the upgraded first stream; and ≤0.1 wt. % of the first stream's ethylene and ≤0.1 wt. % of the first stream's propylene are hydrogenated. It is believed that little or no hydrogenation of the first stream occurs because the $NO_x$/water-removal is conducted at near ambient temperature.

Example 2

Example 1 is repeated except that (i) the $NO_x$ removal agent has a capacity of 0.055%, (ii) the $NO_x$ removal agent's space velocity (GHSV) is 71,504 hr$^{-1}$, and (iii) the $NO_x$ removal agent comprises 10.0 wt. % of the combined weight of the $NO_x$ removal and water removal agents, and the water removal agent comprises 90.0 wt. %.

In this simulation, the upgraded first stream contains ≤1 ppmw of water and ≤1 ppbw (essentially an undetectable amount) of $NO_x$, based on the weight of the upgraded first stream; and ≤0.1 wt. % of the first stream's ethylene and ≤0.1 wt. % of the first stream's propylene are hydrogenated. It is believed that little or no hydrogenation of the first stream occurs because the $NO_x$/water-removal is conducted at near ambient temperature.

These simulations demonstrate that $NO_x$ can be removed to an amount that is sufficient to lessen or even eliminate the risk of an uncontrolled reaction on $NO_x$ gums and/or $NO_x$ salts in a low temperature separation zone, such as one or more cold boxes. Moreover, the examples demonstrate that a conventional water-removal process can be improved, and an upgraded first stream containing <5 ppbw of $NO_x$ produced, by substituting a 5 wt. % to 10 wt. % of the water removal agent with a substantially equivalent amount of a $NO_x$ removal agent and operating the $NO_x$ removal agent at a space velocity (GHSV)≥2.5×10$^4$ hr$^{-1}$.

Example 3

A $NO_x$ removal agent comprising alumina and approximately 16 wt. % Cu, based on the weight of the $NO_x$ removal agent is prepared as follows. PURALOX™ TH 100/150 alumina (Obtained from Sasol North America, Inc., Houston, Tex.) is impregnated with 16.76 wt. % of Cu using incipient wetness impregnation methods disclosed in K. Pansanga, et al., Applied Catalysis A: General 332 (2007) 130-137. The impregnated alumina is exposed to a temperature of 100° C. for 12 hours in order to remove at least a portion of any water from the impregnated alumina. The impregnated alumina is then calcined in air by exposing the impregnated alumina to an increasing temperature from 25° C. to 550° C. at a rate of 5° C./minute, and continuing exposing the impregnated alumina to the 550° C. for three hours to produce a $NO_x$ removal agent precursor.

The $NO_x$ removal agent precursor is activated to become a $NO_x$ removal agent as follows. 300 grams of the precursor is loaded in a tubular vessel, the vessel having an opening at each end for the flow of gas into the vessel via an inlet at one end of the tube, and out of the vessel via an outlet at the opposite end of the tube. The precursor in the tube is exposed to an activating gas of substantially pure molecular hydrogen (≥99 wt. % of molecular hydrogen based on the weight of the activating gas) flowing through the tube from the inlet to the outlet. During activation, the precursor is exposed to an increasing temperature from 25° C. to 246° C. over two hours, while the activating gas flow rate is substantially constant at 165 normal milliliters of activating gas per minute at a total pressure of 35 bar. After the 246° C. temperature is achieved, the precursor exposure to the activating gas at this temperature continues for 24 hours, while maintaining the activating gas flow rate substantially constant at 165 normal milliliters of activating gas per minute and a substantially constant total pressure of 35 bar. After activation, the activated precursor (now a $NO_x$ removal agent) is cooled, but maintained at the 35 bar pressure and the 165 normal milliliters per minute flow rate of activating gas.

Following cooling, a flow of a $NO_x$-containing hydrocarbon feed stream to the tubular vessel at a GHSV of approximately 3×10$^4$ hr$^{-1}$ is substituted for the flow of activating gas. The feed stream comprises 31.6 vol. % ethylene, 36.8 vol. % molecular hydrogen, 36.8 vol. % helium, based on the volume of the feed stream. The feed stream further comprises 300 ppbm of NO, based on the mass of the feed stream. The $NO_x$ removal agent is exposed to a temperature of 15° C. at a total pressure of 35 bar for 48 hours at a substantially constant feedstream GHSV of approximately 3×10$^4$ hr$^{-1}$ ($NO_x$ removal mode). The total effluent conducted away from the vessel is analyzed for NO content, and no detectable NO is observed in the vessel effluent over the two day period. After the 48 hour $NO_x$ removal mode, a regeneration gas (comprising substantially pure molecular hydrogen) is substituted for the feed stream. The $NO_x$ removal agent is exposed to a temperature of 246° C. at a total pressure of 5 bar at a regeneration gas GHSV of about 3.5×10$^4$ hr$^{-1}$ (regeneration mode) for 24 hours. Following the 24 hour regeneration mode, the vessel is operated in $NO_x$ removal mode (the second $NO_x$ removal mode) for 48 hours under substantially the same conditions as in the first $NO_x$ removal mode, and again, no NO is detected in the vessel effluent.

Following the second $NO_x$ removal mode, the vessel is operated in regeneration mode for 24 hours under substantially the same conditions as the first regeneration. Following the second regeneration, the vessel is again operated in $NO_x$ removal mode (the third $NO_x$ removal mode) for 144 hours under substantially the same conditions as in the first $NO_x$ removal mode. No NO is detected in the vessel effluent during the third $NO_x$ removal mode.

This example demonstrates the effectiveness of a $NO_x$ removal agent that is capable of repeatedly removing substantially all of the feed stream's NO at a space velocity $\geq 2.5 \times 10^4$ $hr^{-1}$.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of" "consisting of", "selected from the group of consisting of," or "is" preceding the recitation of the composition, element, or elements and vice versa.

The invention claimed is:

1. A separation process, comprising:
   (a) providing a first stream, the first stream comprising $\geq 1.0$ wt. % methane, $\geq 1.0$ wt. % molecular hydrogen, and $\geq 2.0$ ppbw of $NO_x$, the weight percents being based on the weight of the first stream;
   (b) producing an upgraded first stream by exposing the first stream during a first time interval to a first removal agent to remove $\geq 50.0$ wt. % of the first stream's $NO_x$, based on the weight of the stream's $NO_x$, wherein the first stream contacts the first removal agent at a space velocity (GHSV)$\geq 2.5 \times 10^4$ $hr^{-1}$, and wherein the upgraded first stream comprises <3 ppbw of $NO_x$;
   (c) during a second time interval following the first time interval at least partially regenerating the first removal agent;
   (d) exposing the upgraded first stream to a temperature sufficient to condense at least a portion of the first stream's methane;
   (e) conducting away a second stream, the second stream comprising at least a portion of the condensed methane; and
   (f) conducting away a third stream, the third stream comprising at least a portion of the upgraded first stream's molecular hydrogen.

2. The process of claim 1, wherein:
   (i) the first stream comprises $\geq 10.0$ wt. % methane and $\geq 2.0$ ppbw of NO, and further comprises $\geq 0.05$ mole % water per mole of the first stream;
   (ii) step (b) further comprises exposing the first stream to a second removal agent to remove $\geq 50.0$ wt. % of the first stream's water, based on the weight of the first stream's water, and wherein the first stream contacts the second removal agent at a space velocity (GHSV) $\geq 2.0 \times 10^3$ $hr^{-1}$;
   (iii) $\geq 75.0$ wt. % of the first stream's NO based on the weight of the first stream's NO is removed during step (b); and
   (iv) step (c) further comprises at least partially regenerating the second removal agent during the second time interval.

3. The process of claim 2, wherein the first removal agent comprises $\geq 90.0$ wt. % of at least one solid absorbent and the second removal agent comprises $\geq 90.0$ wt. % of a second solid absorbent.

4. The process of claim 2 wherein (i) the second removal agent is located upstream of the first removal agent with respect to the flow of the first stream during step (b) and (ii) during step (b) the second removal agent removes $\leq 1.0$ wt. % of the first stream's $NO_x$, based on the weight of the first stream's $NO_x$, and the first removal agent removes $\leq 1.0$ wt. % of the first stream's water based on the weight of the first stream's water.

5. The process of claim 1, further comprising producing $\geq 50.0$ wt. % of the first stream based on the weight of the first stream by one or more of hydrocarbon pyrolysis, catalytic cracking of hydrocarbon, dehydrogenation of saturated hydrocarbon, or acetylene hydrogenation.

6. The process of claim 1, wherein the first stream further comprises $\geq 1.0$ wt. % of $C_{2+}$ olefin based on the weight of the first stream.

7. The process of claim 1, further comprising subjecting the first stream upstream of step (b) to one or more of (i) selective hydrogenation, sulfur removal, heavy hydrocarbon removal, water removal, $CO_2$ removal, or CO removal.

8. The process of claim 1, wherein (i) the exposing of step (b) includes a temperature in the range of 4.0° C. to 50.0° C. at a pressure in the range of 13 bar (absolute) to 40 bar (absolute); and (ii) the regenerating of step (c) includes a temperature in the range of 100.0° C. to 400.0° C. and a pressure in the range of 1 bar (absolute) to 10 bar (absolute).

9. The process of claim 1, wherein (i) step (d) includes exposing the upgraded first stream to a temperature $\leq -100.0°$ C.; (ii) the second stream comprises $\geq 50.0$ wt. % of the condensed methane based on the weight of the condensed methane; and (iii) the third stream comprises $\geq 50.0$ wt. % of the upgraded first stream's molecular hydrogen based on the weight of the upgraded first stream's molecular hydrogen.

10. A hydrocarbon upgrading process, comprising:
    (a) providing a first stream comprising $\geq 10.0$ wt. % methane, $\geq 1.0$ wt. % of molecular hydrogen, $\geq 2.0$ ppbw of $NO_x$, the weight percents being based on the weight of the first stream, and $\geq 0.05$ mole % of water per mole of the first stream; and
    (b) during a first time interval exposing the first stream to (i) a second removal agent to remove $\geq 50.0$ wt. % of the first stream's water based on the weight of the first stream's water and (ii) to a first removal agent to remove $\geq 50.0$ wt. % of the first stream's $NO_x$ based on the weight of the mixture's $NO_x$ to produce a first upgraded mixture, wherein the first stream contacts the first removal agent at a space velocity (GHSV)$\geq 2.5 \times 10^4$ $hr^{-1}$, and wherein the upgraded first stream comprises <3 ppbw of $NO_x$.

11. The process of claim 10, further comprising:
    (c) during a second time interval at least partially regenerating the first and second removal agents.

12. The process of claim 11, wherein the exposing of step (b) (ii) is conducted for a time duration $t_1$ and the exposing of step (b)(i) is conducted for a time duration $t_2$.

13. The process of claim 12, wherein the first and second time interval are non-overlapping intervals.

14. The process of claim 12, further comprising:
(d) during the second time interval, exposing the first stream to (i) a fourth removal agent for a time duration $t_4$ to remove ≥50.0 wt. % of the first stream's water based on the weight of the first stream's water and (ii) to a third removal agent for a time duration $t_3$ to remove ≥50.0 wt. % of the first stream's $NO_x$ based on the weight of the mixture's $NO_x$ to produce a second upgraded mixture, wherein the first stream contacts the third removal agent at a space velocity (GHSV)≥2.5×$10^4$ $hr^{-1}$; and
(e) at least partially regenerating the third and fourth removal agents during the first time interval.

15. The process of claim 14, wherein $t_2$ is in the range of $t_1$·0.75 to $t_1$·1.25 and $t_4$ is in the range of $t_3$·0.75 to $t_3$·1.25.

16. The process of claim 14, further comprising combining at least a portion of the first upgraded mixture with at least a portion of the second upgraded mixture.

17. The process of claim 14, wherein ≥90.0% (wt. basis) of the second removal agent is located upstream of ≥90.0% (wt. basis) of the first removal agent and (ii) ≥90.0% (wt. basis) of the fourth removal agent is located upstream of ≥90.0% (wt. basis) of the third removal agent.

18. The process of claim 14, wherein substantially all of (i) the first and (ii) the second removal agents are located in a first vessel, substantially all of (ii) the third and (iii) the fourth removal agents are located in a second vessel, and steps (a) through (e) are operated cyclically.

19. The process of claim 14, wherein the process includes at least one of
(i) the first stream contacts the first removal agent at a space velocity (GHSV)≥5.0×$10^4$ $hr^{-1}$ and $t_2$ is in the range of $t_1$·0.9 to $t_1$·1.1,
(ii) the first stream contacts the third removal agent at a space velocity (GHSV)≥5.0×$10^4$ $hr^{-1}$ and $t_4$ is in the range of $t_3$·0.9 to $t_3$·1.1,
(iii) the first and second time intervals are each ≤100 hours;
(iv) the first and third removal agents comprise a first adsorbent and the second and fourth removal agents comprise a second adsorbent; or
(v) the first adsorbent has a NOx adsorbent capacity ≥0.11 during at least one of $t_1$ or $t_3$.

20. A process for separating a methane-rich stream and a molecular hydrogen-rich stream from a first stream, the process comprising:
(a) providing the first stream, the first stream comprising ≥10.0 wt. % methane, ≥1.0 wt. % molecular hydrogen, and ≥2.0 ppbw of $NO_x$, the weight percents being based on the weight of the first stream, and ≥0.05 mole % of water per mole of the first stream;
(b) producing a first upgraded stream by exposing at least a first portion of the first stream during a first time interval to (i) a second removal agent to remove ≥50.0 wt. % of the first stream's water, based on the weight of the first stream's water, and (ii) a first removal agent to remove ≥50.0 wt. % of the first stream's $NO_x$, based on the weight of the stream's $NO_x$, wherein the first stream contacts the first removal agent at a space velocity (GHSV)≥2.5×$10^4$ $hr^{-1}$, and wherein the upgraded first mixture comprises <3 ppbw of $NO_x$;
(c) at least partially regenerating the first and second removal agents during a second time interval following the first time interval;
(d) conducting at least a portion of the first upgraded stream to a cold box, the cold box being operated under conditions sufficient to condense at least a portion of the first upgraded stream's methane;
(e) removing a second stream from the cold box, the second stream being the methane-rich stream which comprises at least a portion of the condensed methane; and
(f) removing a third stream from the cold box, the third stream being the molecular hydrogen-rich stream which comprises at least a portion of the first upgraded stream's molecular hydrogen.

21. The process of claim 20, further comprising:
(g) producing a second upgraded stream by exposing a second portion of the first stream during the second time interval to (i) a fourth removal agent to remove ≥50.0 wt. % of the second portion's water, based on the weight of the second portion's water, and (ii) a third removal agent to remove ≥50.0 wt. % of the second portion's $NO_x$, based on the weight of the stream's $NO_x$, wherein the first stream contacts the second removal agent at a space velocity (GHSV)≥2.5×$10^4$ $hr^{-1}$;
(h) at least partially regenerating the third and fourth removal agents during the first time interval; and
(i) conducting at least a portion of the second upgraded stream to the cold box.

22. The process of claim 21, wherein (i) the first removal agent comprises ≥1.0 wt. % of at least one Redox agent based on the weight of the first removal agent and/or (ii) the third removal agent comprises ≥1.0 wt. % of at least one Redox agent based on the weight of the third removal agent.

23. The process of claim 21, wherein (i) the first stream further comprises ≥1.0 wt. % of $C_{2+}$ unsaturates based on the weight of the first stream, (ii) the first removal agent comprises ≥1.0 wt. % of one or more of palladium, platinum, or nickel based on the weight of the second removal agent, (iii) the third removal agent comprises ≥1.0 wt. % of one or more of palladium, platinum, or nickel based on the weight of the third removal agent, (iv) ≤1.0 wt. % of the first stream's $C_{2+}$ olefin is hydrogenated during the exposing of step (b) based on the weight of the first stream's $C_{2+}$ olefin, and (v) ≤1.0 wt. % of the first stream's $C_{2+}$ olefin is hydrogenated during the exposing of step (g) based on the weight of the first stream's $C_{2+}$ olefin.

24. The process of claim 21, wherein steps (a)-(i) are operated cyclically.

* * * * *